US006463793B1

(12) United States Patent
Selby

(10) Patent No.: US 6,463,793 B1
(45) Date of Patent: Oct. 15, 2002

(54) EXTENDED RANGE SCANNING BROOKFIELD TECHNIQUES

(76) Inventor: Theodore W. Selby, 4402 Arbor Dr., Midland, MI (US) 48640

( * ) Notice: Subject to any disclaimer, the term of this patent is extended or adjusted under 35 U.S.C. 154(b) by 0 days.

(21) Appl. No.: 09/564,746

(22) Filed: May 4, 2000

Related U.S. Application Data

(60) Provisional application No. 60/132,687, filed on May 5, 1999.

(51) Int. Cl.$^7$ .............................................. G01N 11/14
(52) U.S. Cl. ..................... 73/54.28; 73/54.26; 73/54.32
(58) Field of Search ............................ 73/54.23, 54.26, 73/54.28, 54.32

(56) References Cited

U.S. PATENT DOCUMENTS 5,503,002 A    4/1996  Selby et al. ............... 73/54.28

OTHER PUBLICATIONS

Selby, U.S. provisional application No. 60/067,841.
Selby, U.S. provisional application No. 60/113,576.
Selby, U.S. provisional application No. 60/132,687.
Selby et al., U.S. provisional application No. 60/032,661.
American Society for Testing and Materials, ASTM D 3829–93, 1993.
American Society for Testing and Materials, ASTM D 4684–97, 1997.
American Society for Testing and Materials, ASTM D 5133–96, 1996.
American Society for Testing and Materials, ASTM D 5293–92, 1992.
Appeldoorn, "Motor Oil Viscosity and Cold Starting," API Mtg., Chicago, Nov. 1948; SAE PT–10, pp. 1–6.
Bierylo, "Low–Temperature [Pumping] Deficiencies in Marketed Engine Oils," Proceedings of the 1982 International Conference on the Viscometry of Automotive Lubricants, pp. 65–68, published in 1983 by Savant, Inc.
Chrylser Corp., Engineering Standard No. MS–9767, Jun. 1995.
Cummins Engine Co., Inc., Material Specification No. 20,057–00, May 1985.
Engine Oil Licensing and Certification System, "ILSAC GF–2 Minimum Performance Standard for Passenger Car Engine Oils," Nov. 6, 1995.
Ford Motor Co., Inc., Ford Engineering Material Specification No. WSB–M1C241–A, 1993.
Groh, "Pumpability—Tempus Fugit," Proceedings of the 1982 International Conference on the Viscometry of Automotive Lubricants, pp. 57–64, published in 1983 by Savant, Inc.
Henderson, "Mini–Rotary Viscometer TP–1 Cooling Profile Review," oral presentation handout, 1984 International on the Viscometry of Automotive Lubricants, Gaylord, Oct. 1984.

Henderson et al., "New Mini–Rotary Viscometer Temperature Profiles That Predict Engine Oil Pumpability," SAE Paper No. 850443 (3116R), SAE International Congress and Exposition, Detroit, Feb. 25–Mar. 1, 1985.
Kinker et al., "Evaluation of the Low Temperature Performance of Engine Lubricants Using the Scanning Brookfield Viscometer," 11th International Colloquium on Tribology, Stuttgart, Jan. 13–15, 1998.
McGeehan et al., "The Pivotal Role of Crankcase Oil in Preventing Soot Wear and Extending Filter Life in Low Emission Diesel Engines," SAE Paper No. 1999–01–1525, International Spring Fuels and Lubricants Meeting and Exposition, Dearborn, May 3–6, 1999.
McMillan et al., "The Relationship of Low–Temperature Rheology to Engine Oil Pumpability," SAE Paper No. 730478 (SP–382), Viscosity and Its Application to Automotive Lubricants, SAE National Automobile Engineering Meeting, Detroit, May 14–18, 1973.
Resio et al., A New Instrumental Approach to the Determination of Yield Stress of Engine Oils and Other Lubricants, 1997 SAE International Spring Fuels and Lubricants Meeting, Dearborn, May 5–8, 1997.
Resio et al., "The Critical Third Zone—A New, Fast Method of Measuring Engine Oil Pumpability a Low Temperatures from Pump to Lubrication Site," SAE Paper No. 981411 (peer review copy), SAE International Spring Fuels and Lubricants Meeting, Dearborn, May 4–6, 1998, paper presented on May 5, 1998.
Rhodes, "Assessment of the Low–Temperature Incompatibility Risk of Commercial Engine Oils," SAE Paper No. 941976 (SP–1055), SAE 1994 Transactions, Journal of Fuels & Lubricants, Section 4, pp. 1342–1351.
Rhodes, "Low–Temperature Compatibility of Engine Lubricants and the Risk of Engine Pumpability Failure," SAE Paper No. 932831 (SP–996), SAE Fuels and Lubricants International Fall Conference, Philadelphia, Oct. 18–20, 1993.
Rhodes et al., personal correspondence received on Apr. 9, 1997.
Savant, Inc., Lubrication Technology, May 1998, pp. 1, 2 & 4.
Selby, "A Comparison of the Effects of Cranking Speed and Oil Viscosity on Low–Temperature Engine Starting," SAE Paper No. 640427 (805C), SAE Automotive Engineering Congress, Detroit, Jan. 1964.

(List continued on next page.)

Primary Examiner—Daniel S. Larkin
(74) Attorney, Agent, or Firm—Christopher John Rudy

(57) ABSTRACT

Physical property of a liquid sample to include a viscometric and/or rheological property if not a structural property such as gelation and/or crystallization can be determined with a rotating viscometer employed in a Scanning Brookfield technique. The viscometer and technique employ a Brookfield-type head having a high torque capacity. Low temperatures may be employed in the scan. For example, properties of a motor oil having a very high viscosity and/or a gelation point owing to its intrinsic properties, oxidation and/or sooting and so on, can be accurately, precisely, rapidly, and repeatably determined.

17 Claims, 25 Drawing Sheets

OTHER PUBLICATIONS

Selby, "A discussion of a paper by R.L. Stambaugh and J.H. O'Mara, Rohm & Haas Co., entitled: 'Low Temperature Flow Properties of Engine Oils,' given at the 1982 SAE International Congress, Feb. 22–26," published as Annex 4 to ASTM Research Report No. D02–1261 for the Scanning Brookfield Technique, Approved by ASTM, Oct. 26, 1990.

Selby, "Further Considerations of Low–Temperature, Low–Shear Rheology Related to Engine Oil Pumpability—Information from the Scanning Brookfield Technique," SAE Paper No. 852115, SAE International Fuels and Lubricants Meeting and Exposition, Toronto, Nov. 2–5, 1985.

Selby, "Problems in Bench Test Prediction of Engine Oil Performance at Low Temperature," SAE Paper No. 922287 (SP–986), SAE International Fuels & Lubricants Meeting and Exposition, San Francisco, Oct. 19–22, 1992.

Selby, "Pumpability—Past Accomplishments; Present and Future Challenges," draft, publication expected 2000 A.D., topic presented orally Jun. 1999.

Selby, "Recent Developments in Testing Lubricants," 6th International LFE Congress, Brussels, Jun. 2–4, 1999.

Selby, "The Scanning Brookfield Technique of Low–Temperature, Low–Shear Rheology—Its Inception, Development, and Applications," in Rhodes (Ed.), Low–Temperature Lubricant Rheology Measurement and Relevance to Engine Operation, ASTM STP 1143, ASTM Committee D–2, Subcommittee 7, Lubricant Flow Properties, Austin, Dec. 10, 1991.

Selby, "The Use of the Scanning Brookfield Technique to Study the Critical Degree of Gelation of Lubricants at Low Temperature," SAE Paper No. 910746, SAE International Congress and Exposition, Detroit, Feb. 25–Mar. 1, 1991.

Selby, "Viscosity and the Cranking Resistance of Engine Oils at Low Temperatures," 6th World Petroleum Congress Proceedings, Section VI, Frankfurt, Jun. 1963, pp. 241–258.

Shaub et al., "Mini–Rotary Viscometer and Engine Oil Pumpability," STLE 35th Annual Meeting, Anaheim, May 5–8, 1980.

Shaub et al., "Predicting Low Temperature Engine Oil Pumpability with the Mini–Rotary Viscometer," SAE Paper No. 790732, SAE Passenger Car Meeting, Dearborn, Jun. 11–15, 1979.

Sheahan, Letter to Messrs. Houubec and Duffy, May 29, 1992.

Smith, Jr., "Better Prediction of Engine Oil Pumpability Through a More Effective MRV Cooling Cycle," SAE Paper No. 831714, SAE Fuels and Lubricants Meeting, San Francisco, Oct. 31–Nov. 3, 1983.

Stambaugh et al., "Low–Temperature Flow Properties of Engine Oils," SAE Paper No. 820509, SAE International Congress and Exposition, Detroit, Feb. 22–26, 1982.

Stewart et al., "Summary of ASTM Activities on Low Temperature Engine Oil Pumpability," SAE Paper No. 821206, SAE Fuels and Lubricants Meeting, Toronto, Oct. 18–21, 1982.

Stewart et al., "The Relationship Between Oil Viscosity and Engine Performance—A Literature Search," SAE Paper No. 770372 (SP–416), in Stewart et al. (Eds.), The Relationship Between Engine Oil Viscosity and Engine Performance, SAE, 1977, pp. 1–19.

Wheeler et al. (Eds.), "Low–Temperature Pumpability Characteristics of Engine Oils in Full–Scale Engines," ASTM Data Series DS 57, Data Analysis Panel RDD 7C, ASTM, Sep. 1975.

Wright, An Improved Viscosity–Temperature Chart for Hydrocarbons, Journal of Materials, JMLSA, vol. 4, No. 1, 1969, pp. 19–27.

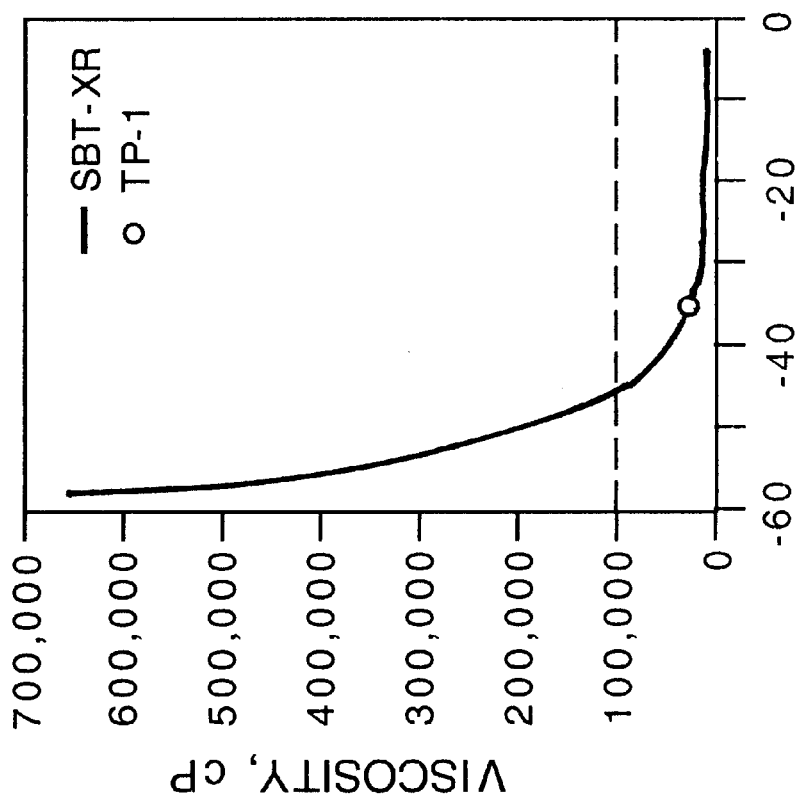
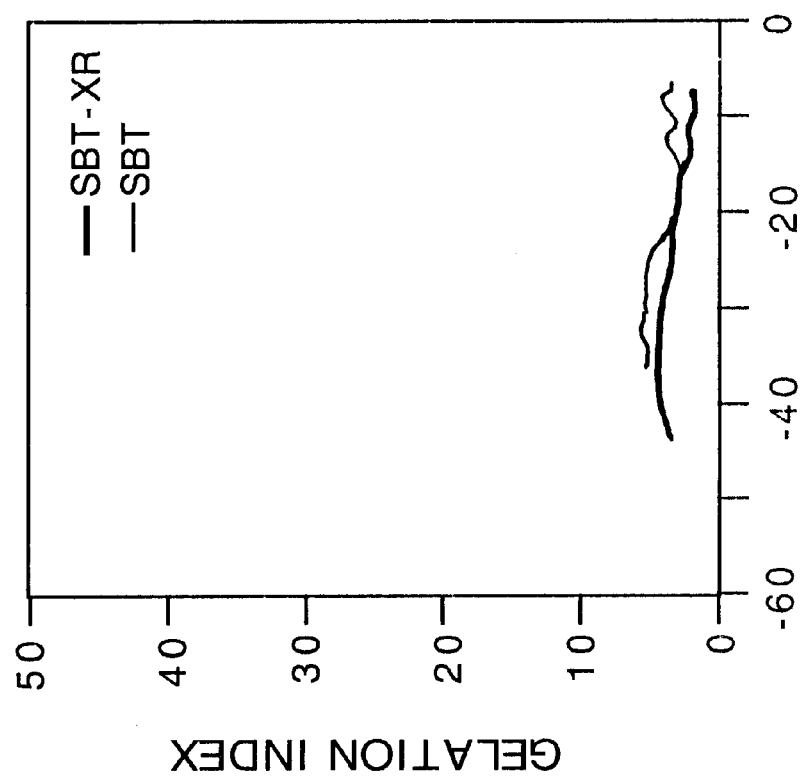

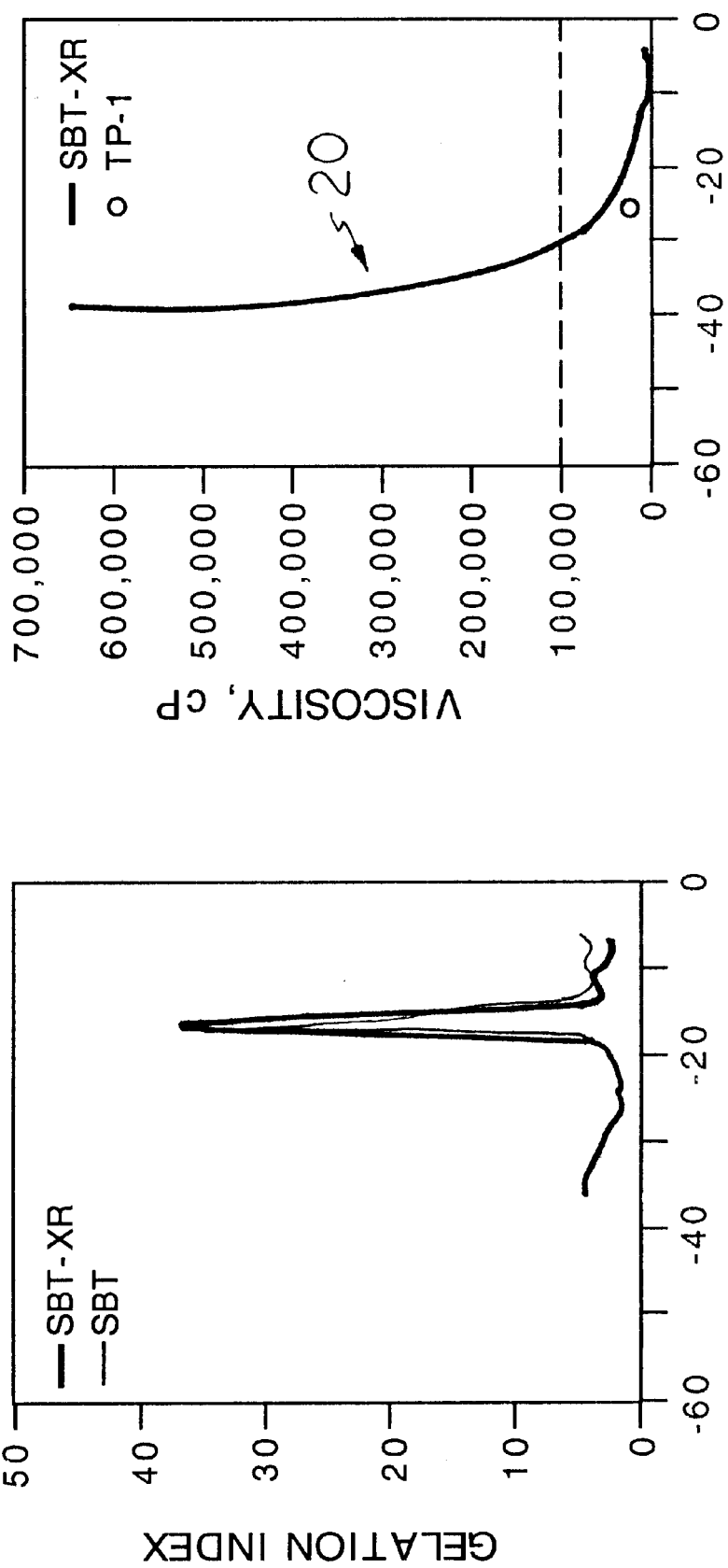

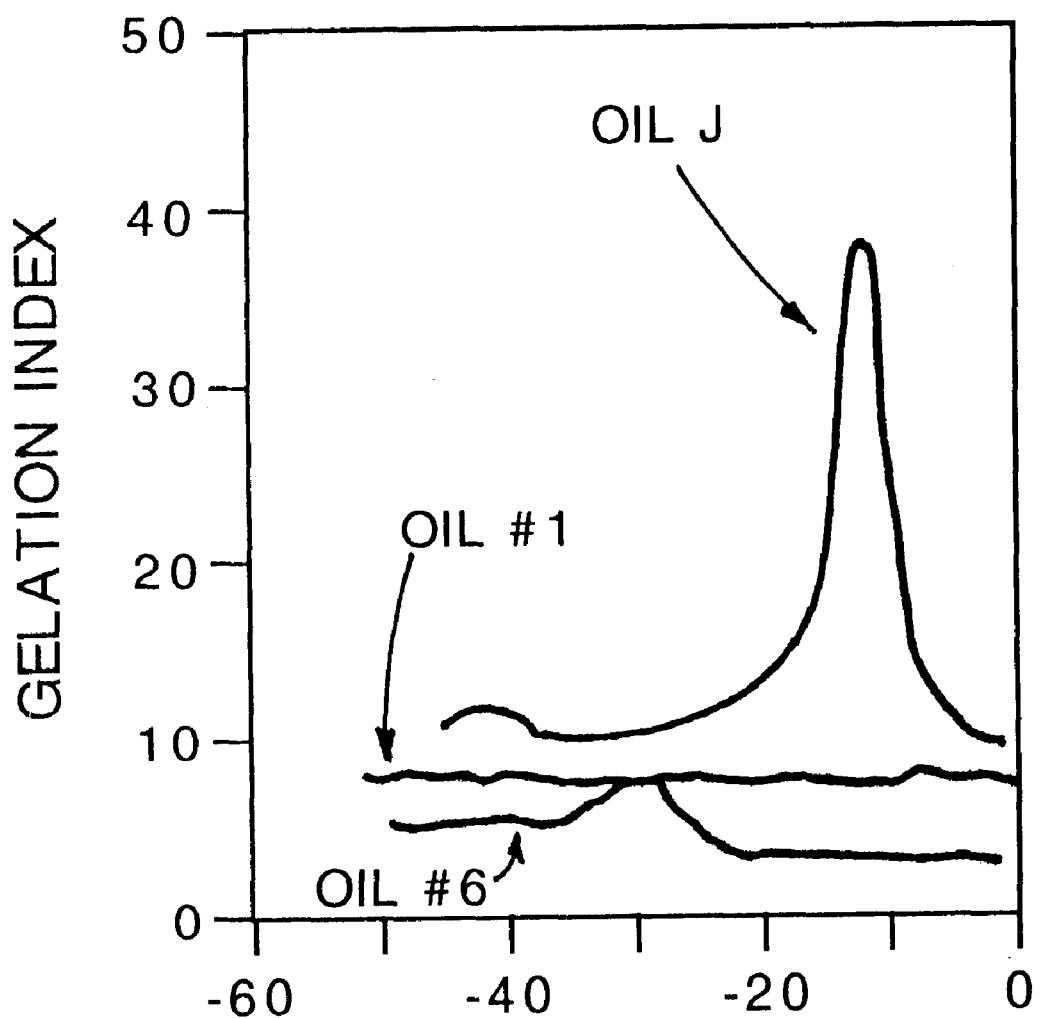

EXTENDED RANGE SCANNING BROOKFIELD TECHNIQUES

This claims benefit under 35 USC 119(e) of U.S. provisional patent application No. 60/132,687 filed on May 5, 1999 A.D.

FIELD AND PURVIEW OF THE INVENTION

The present invention concerns a method of determining a physical property of a liquid sample to include a viscometric and/or Theological property if not a structural physical property such as gelation and/or crystallization, which employs a rotating viscometer, especially a Scanning Brookfield Viscometer technique which employs a Brookfield-type head having a high torque capacity; as well as a device useful for carrying out the same, which is the Brookfield-type head having the high torque capacity in combination with temperature-scanning equipment. In essence, the invention provides ways and means to measure low and/or high temperature viscosity of a liquid, for example, a motor oil having a very high viscosity and/or a gelation point owing to its intrinsic properties, oxidation and/or sooting and so on, with an accuracy, precision, rapidity, and repeatability heretofore unknown in the art, as well as provide data heretofore inaccessible or unknown in the art, by employment of a temperature-scanning technique.

BACKGROUND TO THE INVENTION

I. In General

Standard Scanning Brookfield techniques are well known in the field of viscometry and rheology. See, e.g., ASTM D 5133-96. In general, the standard Scanning Brookfield technique (SBT) is a method in viscometric testing for determining certain characteristics and parameters of fluids, for example, engine oils. Many of the standard runs vary the temperature from zero to minus forty degrees C, with small incremental changes in temperature over two to three days. Some, however, expand the temperature range, say, from +25 to −70 degrees C. See, Savant, Inc., *Lubrication Technology*, May, 1998, pages 1, 2 and 4. Note, Selby et al., U.S. patent application Ser. No. 09/032,661 (abandoned) which discloses how the jet fuels and the like low viscosity liquids can be analyzed. In the standard techniques, however, very high viscosity liquids are found to be poor candidates for the techniques, if they can be considered to be effectively characterized at all. In fact, the ASTM D 5133 method cannot provide all data necessary for engine lubrication fluids under all operating conditions. For example, in internal combustion engine operation, fluid operation characteristics concerning the region of fluid operation in the so-called "Third Zone," i.e., from the pump to the lubrication site, are being recognized as a critical area of concern in lubricant performance.

Nevertheless, in the ever more sophisticated art of lubricant characterization and employment, very high viscosity liquids come more and more under consideration. High viscosity and gelation of lubricating oil, for example, can be of critical concern not only when exposed to very low temperature environments but also in higher temperature environments when the engine oil is highly loaded with engine soot, when the engine oil is highly oxidized, or both. And yet, efficient test methodology is lacking in this critical area, which can be employed to predict lubrication fluid performance—before engine breakdown may occur as a result of the use of an inadequate lubricant.

Actually, engine oils which show classic gelation in sensitive bench test devices developed to correlate with field-failing oils show little or no evidence of gelation effects in fairly recent ASTM cold-room pumpability work. In addition to raising questions about the meaning of the pumpability results, this has led to difficulty in developing correlations between results from the engines and the bench-test sources of low-temperature data.

Brookfield-type rotational viscometer heads having low, medium, high and very high sensitivities are known. See, TABLE 1, infra. The medium, high and very high sensitivity models, in particular, are heretofore known to be employed in set, single-temperature settings, and data and correlations obtained therefrom are limited.

II. Brief History

Pumpability of engine oils at low temperatures has been an ongoing concern for a number of years, particularly for engine manufacturers who have seen pumpability problems as increasing their burden of warranty costs. See, Appeldoorn, "Motor Oil Viscosity and Cold Starting," API Mtg., Chicago, November, 1948; SAE PT-10, pp. 1–6; Selby, "Viscosity and the Cranking Resistance of Engine Oils at Low Temperatures," 6th World Petroleum Congress Proceedings, Section VI, Frankfurt, June, 1963, pp. 241–258; McMillan et al., "The Relationship of Low-Temperature Rheology to Engine Oil Pumpability," SAE Paper No. 730478 (SP-382), Viscosity and Its Application to Automotive Lubricants, SAE National Automobile Engineering Meeting, Detroit, May 14–18, 1973; Groh, "Pumpability—Tempus Fugit," Proceedings of the 1982 International Conference on the Viscometry of Automotive Lubricants, pp. 57–64, published 1983 by Savant, Inc., and Bierylo, "Low-Temperature Deficiencies in Marketed Engine Oils," Proceedings of the 1982 International Conference on the Viscometry of Automotive Lubricants, pp. 65–68, published 1983 by Savant, Inc. While either the engine oil or the engine design (or a combination of both) may be the primary cause, the extensive damage that can ensue from a lack of sufficient oil supply to highly loaded lubrication sites in the engine often obscures any role of the oil. Oil-induced pumpability failure thus places warranty costs on the engine manufacturer unless there is an epidemic of failures identifying a common oil linkage.

An emphasis has been placed on lower SAE W-Graded engine oils

For several years engine manufacturers have encouraged the use of lower viscosity, multi-grade engine oils such as SAE 5W30 and 10W30. Reasons given have been a quicker supply of oil to lubrication sites at low temperature as well as fuel efficiency benefits. This direction of technical development would seem to also improve rapidity of lubricant flow in the engine on start-up at low temperatures.

Highly refined, hydro-treated base stocks have aided such development but also brought about the need to treat the increased paraffinic content of these highly refined mineral oil base stocks carefully with pour-point depressants. Such oils can be very sensitive to type and concentration of the pour-point depressant and thus require careful monitoring in production to avoid misblends having significant gelation. See, Kinker et al., "Evaluation of the Low Temperature Performance of Engine Lubricants Using the Scanning Brookfield Viscometer," 11th International Colloquium on Tribology, Stuttgart, Jan. 13–15, 1998.

Additionally, it has been shown that even mixing brands of engine oils can produce gelation as a result of the interaction of viscosity index (VI) Improvers in one lubricant with the pour-point depressant and paraffinic content of another oil. See, Rhodes, "Low-Temperature Compatibility of Engine Lubricants and the Risk of Engine Pumpability Failure," SAE Paper No. 932831 (SP-996), SAE Fuels and Lubricants International Fall Conference, Philadelphia, Oct. 18–20, 1993; Rhodes, "Assessment of the Low-Temperature Incompatibility Risk of Commercial Engine Oils," SAE Paper No. 941976 (SP-1055), SAE 1994 Transactions, Journal of Fuels & Lubricants, Section 4, pp. 1342–1351.

III. Heretofore Known Status of Pumpability Studies

At low ambient temperatures, the importance of rapidly supplying engine oil to lubrication sites in the engine has led to incorporating pumpability limits in SAE J300 as well as the establishment of firm specifications by automotive engine manufacturers limiting the level of engine oil gelation as measured by the so-called Gelation Index. These specifications have been applied to engine oils used both internally (factory fill) and internationally. See, Ford Motor Co., Inc., Ford Engineering Material Specification WSB-M1C241-A, 1993; Chrysler Corp., Engineering Standard No. MS-9767, June, 1995; Cummins Engine Co., Inc., Material Specification No. 20,057-00, May, 1985; Engine Oil Licensing and Certification System, "ILSAC GF-2 Minimum Performance Standard for Passenger Car Engine Oils," Nov. 6, 1995.

More critically for the engine manufacturer is the possibility that borderline pumpability conditions may result in progressive damage to engine components which only show up as abbreviated engine life. With today's 100,000-mile extended warranties for the consumer, this again translates to higher warranty costs—albeit at higher mileages.

As just mentioned, an epidemic of failures in a short period of time at a given location brings attention to the role of the engine oil. This was the situation in Sioux Falls, S.D., several years ago, and is known as "The Sioux Falls Incident."

During the winter of 1980–1981, a certain weather condition produced an oil rheology in at least one brand of oil causing failure in a number of engines. Even in this case, the cause triggering the failures was not clearly identified until careful research in cold-room engine studies revealed that the engine oil would, under certain cooling conditions, become highly gelated. See, Stambaugh et al., "Low Temperature Flow Properties of Engine Oils," SAE Paper No. 820509, SAE International Congress and Exposition, Detroit, Feb. 22–26, 1982.

On starting the engine, this produced a condition called 'air-binding' (cf. FIG. 1) in which the oil pump pulls a vortex of air from the oil surface.

Since that time, the nature of pumpability failure and pumpability tests—both on the laboratory bench and in cold-room engines—have been a major focus of study, discussion, and specification development. See, Stewart et al., "The Relationship Between Oil Viscosity and Engine Performance—A Literature Search," SAE Paper No. 770372 (SP-416), in Stewart et al. (Eds.), The Relationship Between Engine Oil Viscosity and Engine Performance, SAE, 1977, pp. 1–19.

Advances in startability have an impact on pumpability. More recently, as a result of advances in easing engine startability at low temperatures, pumpability has emerged as the most critical low-temperature lubrication problem. See, Selby, "Problems in Bench Test Prediction of Engine Oil Performance at Low Temperature," SAE Paper No. 922287 (SP-986), SAE International Fuels and Lubricants Meeting and Exposition, San Francisco, Oct. 19–22, 1992. With higher horsepower generated in smaller engines, the need to rapidly get lubricant to the critical lubrication sites before wearing conditions intensify is even more critical—particularly at low temperatures when the oil is most viscous and resistant to flow.

The question of pumpability in modern engines has been renewed.

In 1992, with no significant evidence of pumpability problems for a decade, questions were raised regarding the continued need for, relevance of, and startability relationship with, pumpability and gelation. Subsequently, a letter was written by the Chairman of the SAE Fuels and Lubricants Committee to the appropriate level of ASTM Committee D-2 requesting that the subjects of pumpability, startability, their interrelationship, and their instrument dependence be revisited. Note, Sheahan, Letter to Messrs. Houubec and Duffy, May 29, 1992, which discusses evolution of low-temperature viscosity requirements in the Engine Oil Viscosity Classification SAE J300, and requests ASTM to conduct a low-temperature study of the cranking, starting, and pumping requirements of modern engines.

The 'if start, must pump' concern is an important concern, which is to assure that an oil's pumpability would be sufficient to satisfy the lubrication needs of a modern engine after it was started and running at low ambient temperatures. With fuel injection and electronic ignition, these engines were capable of starting at considerably lower temperatures and higher viscosities than in the early 1960s. Partially because of one difficult-to-start engine as reported by Selby, "A Comparison of the Effects of Cranking Speed and Oil Viscosity on Low-Temperature Engine Starting," SAE Paper No. 640427 (805C), SAE Automotive Engineering Congress, Detroit, January, 1964 (but also because of results of a number of other studies as reported in the SAE Paper No. 770372), 3500 centipoise (cP) had been established as a maximum low-temperature viscosity for the most widely used SAE multi-grade engine oils (i.e., those carrying 5W-, 10W-, or 15W-'X' as part of their SAE viscosity classification).

The ASTM response to the SAE request was to immediately conduct an ASTM starting and pumping study through formation of a Low-Temperature Engine Pumpability (LTEP) Task Force under Subcommittee 7 of ASTM Committee D-2. This task force had the responsibility of meeting the SAE request by conducting relevant cold-room starting and pumpability studies with modern engines and correlating the latter with the bench instruments being used.

A number of automotive, petroleum, and additive engineers and scientists joined this Task Force—several of whom had served on the first Pumpability Task Force of the 1970s.

Three needs were evident once cold-room facilities were selected. These needs were identified as follows:

1. choose appropriate test engines;
2. develop cold-room techniques emulating what nature might do to produce field gelation conditions in the sump; and
3. obtain or make engine oils which would have a suitable range of gelating tendency (air-binding response). (The other form of pumpability failure through viscous pumping difficulties, or 'flow-limited' behavior, could be readily induced without special cooling techniques.)

Startability issues were addressed. Startability study protocols were relatively easily established and reasonably straightforward—cooling time, temperatures of test, cranking duration, frequency of attempted restart, battery condition, test data to be gathered, etc., were the primary factors and issues considered.

Pumpability issues were considered. Pumpability issues, on the other hand, required much more thought and discussion. Test protocols were needed that might be successful in producing gelation in the cold-room with the hope of anticipating and imitating low-temperature weather anomalies in nature.

Bench test correlation issues were assessed. As previously noted, a further part of the request by the SAE was to assess the bench tests used in pumpability measurements to determine how they correlated with pumpability failures in engines. A basic question was raised during early discussions whether to first prove an engine test protocol that would display air-binding or to try three or four protocols on several test oils and to accept the engine response whether or not air-binding was displayed. The latter path, which was decided upon, was less time-consuming and costly but, if air-binding were not shown in the cold-room tests, also less persuasive as being imitative of nature.

IV. Background in Bench Tests

The MRV and ASTM D 3829 methods were developed.

One of the primary reasons for care and concern in developing pumpability tests by the LTEP Task Force was the memory of the prior ASTM cold-room engine pumpability studies in the 1970s. The information from these earlier cold-room pumpability tests was used to develop an instrument capable of showing good correlation with those same engine pumpability tests. This instrument was called the Mini-Rotary Viscometer (MRV) and was accepted as the ASTM Test Method D 3829 in 1979. See, Low-Temperature Pumpability Characteristics of Engine Oils in Full-Scale Engines, ASTM Data Series DS 57, Data Analysis Panel, RDD 7C, Ed., ASTM, 1995; H. Schaub, M. F. Smith, and C. K. Murphy, "Predicting Low Temperature Engine Oil Pumpability with the Mini-Rotary Viscometer," SAE Paper No. 790732, SAE Passenger Car Meeting, Dearborn, Mich., Jun. 11–15, 1979; H. Schaub and C. K. Murphy, "Mini-Rotary Viscometer and Engine Oil Pumpability," STLE 35th Annual Meeting, Anaheim, Calif., May 5–8, 1980; ASTM Standard Test Method D 3829-93, "Predicting the Border-Line Pumping Temperature of Engine Oil," 1998 Annual Book of ASTM Standards, Section 5, Vol. 05.02, ASTM, 1998, pp. 595–599.

The Sioux Falls Incident had an impact.

The cold-room engine tests of the first ASTM pumpability study were as well-conceived and engineered as the limited pumpability knowledge of that time would permit. However, as happens all too frequently in efforts to anticipate the vagaries of nature, the conclusions from this earlier study were swept aside by the later episode of engine failures in Sioux Falls caused by a set of weather conditions producing air-binding response mentioned earlier. This failing condition of the oils was not indicated by Method D 3829.

In retrospect, it was recognized that the cold-room engine pumpability test protocols used were only a part of a much larger population of possible test protocols—any number of which might be reasonably encountered in nature.

Efforts were made to develop correlative instruments.

The availability of field-failing engine oils was an opportunity to develop new approaches to the bench measurement of pumpability-related oil rheology.

In 1981, a different form of bench test was developed, the SBT. See, Selby, "A discussion of a paper by R. L. Stambaugh and J. H. O'Mara, Rohm & Haas Co., entitled: 'Low Temperature Flow Properties of Engine Oils,' given at the 1982 SAE International Congress, Feburary 22–26," published as Annex 4 to ASTM Research Report No. D02-1261 for the Scanning Brookfield Technique, Approved by ASTM, Oct. 26, 1990. The test was shown to be gelation-sensitive, and was later shown capable of direct measure of gelation intensity by calculation of the Gelation Index, a method of measuring the strength and extent of gelation. See, Selby, "The Scanning Brookfield Technique of Low-Temperature, Low-Shear Rheology—Its Inception, Development, and Applications," in Rhodes (Ed.), Low-Temperature Lubricant Rheology Measurement and Relevance to Engine Operation, ASTM STP 1143, ASTM Committee D-2, Subcommittee 7, Lubricant Flow Properties, Austin, Dec. 10, 1991; Selby, "Further Considerations of Low-Temperature, Low-Shear Rheology Related to Engine Oil Pumpability—Information from the Scanning Brookfield Technique," SAE Paper No. 852115, SAE International Fuels and Lubricants Meeting and Exposition, Toronto, Nov. 2–5, 1985; Selby, "The Use of the Scanning Brookfield Technique to Study the Critical Degree of Gelation of Lubricants at Low Temperature," SAE Paper No. 910746, SAE International Congress and Exposition, Detroit, Feb. 25–Mar. 1, 1991; ASTM D 5133-96. This SBT protocol required a 1° C./hour continuous scan of the oil's viscosity over the low temperature range likely to be encountered.

Regarding the MRV, strong efforts were made to revise its test protocol over the five years following The Sioux Falls Incident. After the dedicated efforts of several investigators, in 1987 a revised MRV technique, code-named TP-1, was established. Note, Stewart et al., "Summary of ASTM Activities on Low Temperature Engine Oil Pumpability," SAE Paper No. 821206, SAE Fuels and Lubricants Meeting, Toronto, Oct. 18–21, 1982; Smith, Jr., "Better Prediction of Engine Oil Pumpability Through a More Effective MRV Cooling Cycle," SAE Paper No. 831714, SAE Fuels and Lubricants Meeting, San Francisco, Oct. 31–Nov. 3, 1983; Henderson, "Mini-Rotary Viscometer TP-1 Cooling Profile Review," oral presentation handout, 1984 International on the Viscometry of Automotive Lubricants, Gaylord, October 1984; Henderson et al., "New Mini-Rotary Viscometer Temperature Profiles That Predict Engine Oil Pumpability," SAE Paper No. 850443 (3116R), SAE International Congress and Exposition, Detroit, Feb. 25–Mar. 1, 1985; ASTM D 4684-97. In contrast to the SBT, the MRV cools the sample quiescently and, thus, produces one value per test at the temperature of interest.

Both instruments require extended cooling—25 hours from −5° to −30° C. for the SBT; 46 hours from −5° to −30° C. for the MRV.

V. New Pumpability Challenges

Recent developments regarding passenger car engine oil were made. The combination of highly paraffinic base oils, need for careful selection of pour-point depressants, and the influence of the other additives has placed a premium on good pumpability of the oil and the additional impact of other additive chemistry introduced when the crankcase is topped up with a different engine oil. The latter factor was studied and reported in papers by Rhodes in 1993 and 1994. Note, the SAE Paper Nos. 932831 and No. 941976.

Essentially, it appears that with the development of more highly paraffinic base oils, the careful balance of the base oil, the pour-point depressant, the VI Improver, and the additive package must not only be obtained for the fresh oil but maintained in the used oil during its life in the engine. This of course brings in the effects of base stock and additive exposure to oxidation and, extending the above observations by Rhodes, the potential impact of oil admixtures between drain intervals. In turn, these effects must be coupled with the degree of oxidation and viscosity increase imposed by longer drain intervals.

Recent developments regarding heavy duty diesel engine oil were made. Another impact on low-temperature pumpability has been encountered recently in the area of heavy duty diesel engines. Note, McGeehan et al., "The Pivotal Role of Crankcase Oil in Preventing Soot Wear and Extending Filter Life in Low Emission Diesel Engines," SAE Paper No. 1999-01-1525, International Spring Fuels and Lubricants Meeting and Exposition, Dearborn, May 3–6, 1999.

Government requirements for major reduction in the emission of oxides of nitrogen from these engines has resulted in retarding the combustion cycle with the result that large quantities of soot are generated. This soot rapidly loads the engine oil to levels of 10% and higher. The effect of such high soot loading on the action of dispersant additives and the strong possibility that lack of control of such soot levels could adversely affect pumpability even at higher ambient temperatures is a serious concern.

VI. Desires and Needs in the Art

It would be desirable for effective lubrication to be able to provide adequate lubrication and freedom from oil gelation. Moreover, in line with the same, it would be desirable to be able to ascertain under laboratory conditions those lubricants which are so effective.

SUMMARY OF THE INVENTION

The present invention provides, in one aspect, a method for determining a physical property of a liquid sample, i.e., a test fluid, such as a viscometric and/or rheological property as well as a structural physical property such as gelation and/or crystallization, which employs an extended range rotating viscometer technique comprising: providing a suitable rotary viscometer with a rotor and a stator and having a suitably strong head, preferably a Brookfield-type viscometer, which includes a motor driving a rotor, a stator in which the test fluid is to be contained, with the rotor being driven in the test fluid in the stator, and a temperature-control feature which can control the temperature of the test fluid in the stator during testing; providing the test fluid to the stator, and immersing the rotor in the test fluid in the stator; rotatably contacting the rotor with the sample in the stator by driving the rotor immersed in the test fluid with the motor, typically under high shear stress conditions, while varying temperature of the temperature-control feature, and hence, the test fluid, as a function of time. Advantageously, the temperature is varied over a period of about half a day or less, for Third Zone correlations, and slower cooling (e.g. one degree Celsius per hour or less) for First Zone correlations, with temperature being lowered throughout the testing from and to a suitably low value; monitoring the stress and/or viscosity of the test fluid during the testing by measuring drag on the rotating rotor; and obtaining data therefrom. Also provided is a rotary viscometer device useful for carrying out the method.

The invention is useful in materials characterization, and especially in determining lubrication characteristics. In particular, it is useful to determine and predict lubricant characteristics in the "First and Third Zones."

Significantly, the invention is a breakthrough in the field, particularly with respect to modem engine oil testing. Hereby, improvements in kind are provided the art for dramatically better characterizations of higher viscosity liquids and of the liquids as when classical structural characteristics such as gelation or crystallization develop. In particular, the invention makes it possible to characterize and compare such liquids and differentiate the effects of additive systems to control gelation and crystallization. Notably, with this invention, the differences of additive treatments to better disperse soot and to prevent soot-agglomeration as well as of oxidation inhibitors to prevent oxidation of the oil from causing low temperature pumpability problems can be determined. For the first time in the art, a relatively quick, highly efficient and reliable test method is made available to determine and predict engine oil performance in the newly recognized, critical region of performance from the oil pump to the lubrication site. Data pertinent to these "First and Third Zones" is now found to be so necessary in evaluating oils and other liquid lubricants for performance in modem engines in temperate zone winter and arctic environments By this invention, accuracy, precision, rapidity, and repeatability heretofore unknown, as well as data heretofore inaccessible or unknown, is provided to the art in the test fluids of interest.

Surprisingly, sensitivity is satisfactory if not actually increased in the highly viscous or gelating liquid samples by employing the higher strength heads in the practice of the invention. This is contrary to that wisdom which had been believed or propounded by those ordinarily skilled or even expert in the art in that a rotary viscometer head having a high torque or a sensitivity of greater than seventy Pascals (Pa) would be ineffective in determining viscosity.

Numerous further advantages attend the invention.

DRAWINGS AND EXPLANATIONS THEREOF

The drawings form part of the specification hereof. With respect to the drawings, the following is noted:

FIG. 1 is a side plan view of engine regions affected by pumpability, showing the three zones of shear stress imposed by engine operation. Zone No. 1 is from engine oil sump 10 to oil pickup screen 11 at oil pump inlet 12, where, under certain adverse conditions, air-binding may occur at site 13; Zone No. 2 is from the screen 11 to engine oil pump 14; and Zone No. 3 is from the pump 14 through engine oil galleys 15.

Figure 5:
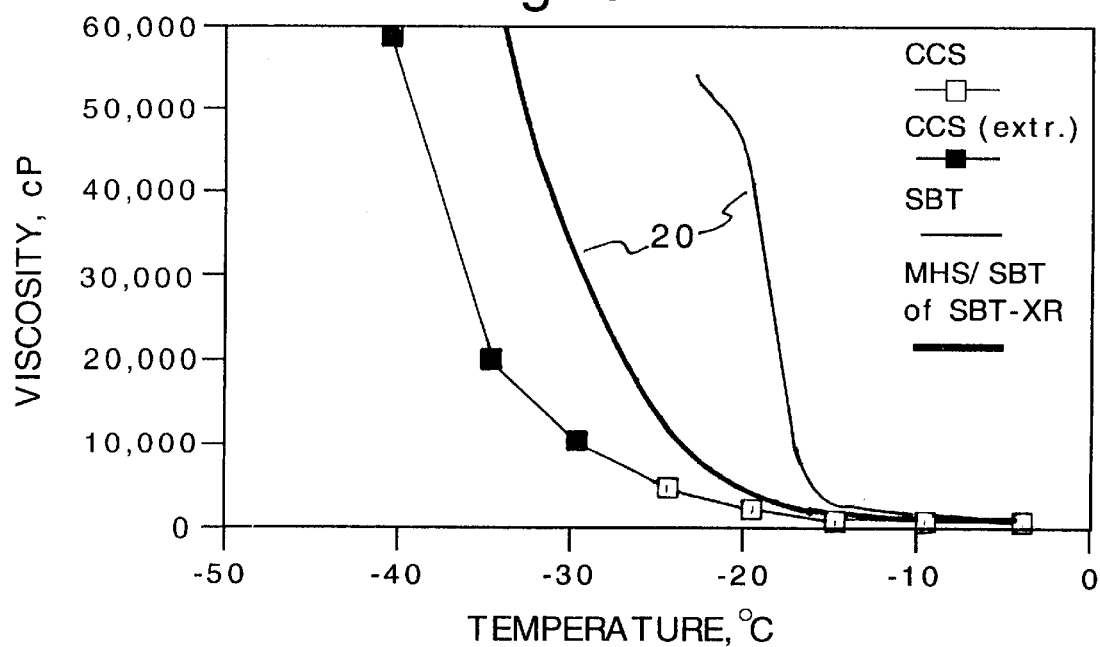

FIG. 5 is a graph showing viscosity-temperature plots at low temperatures using three instruments, Cold Cranking Simulator (CCS) as well as extrapolations of CCS values (CCS(extr.)); SBT; and SBT extended range (SBTXR) of the invention using moderately high shear stress SBT (MHS/SBT), applying different shear stress with LTEP-28, a gelating oil. Note, "ogee" curves 20.

Figure 6:
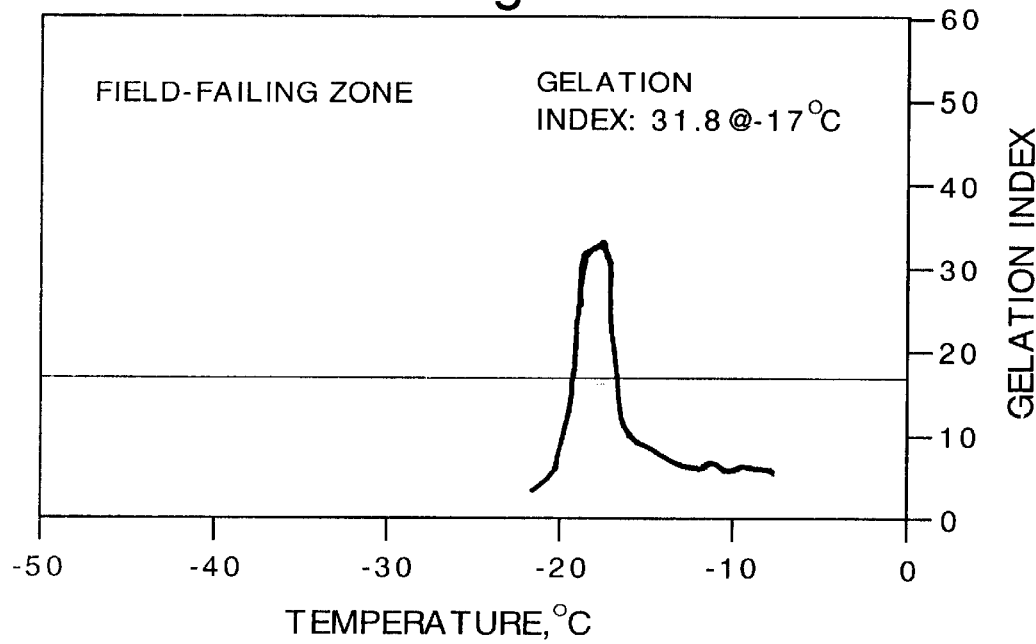

FIG. 6 is a graph showing gelation index and gelation index temperature of the LTEP-28 oil at low shear stress, using ASTM D 5133 low shear stress SBT analysis.

Figure 7:
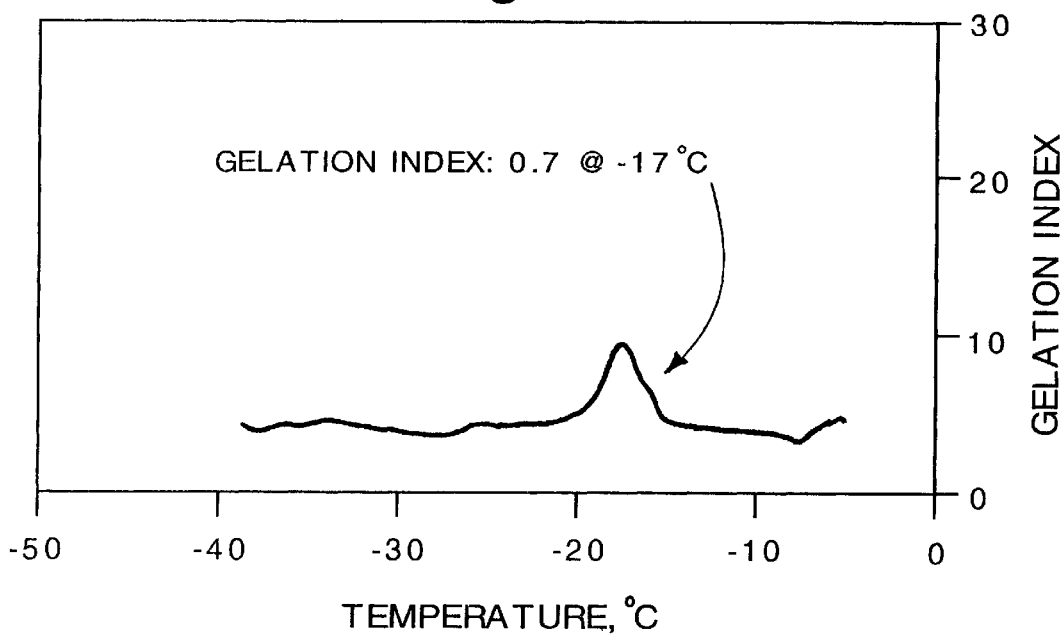

FIG. 7 is a graph showing gelation index and gelation index temperature of the LTEP-28 oil at moderately high shear stress, using MHS/SBT of SBT-XR of the invention.

Figure 8:
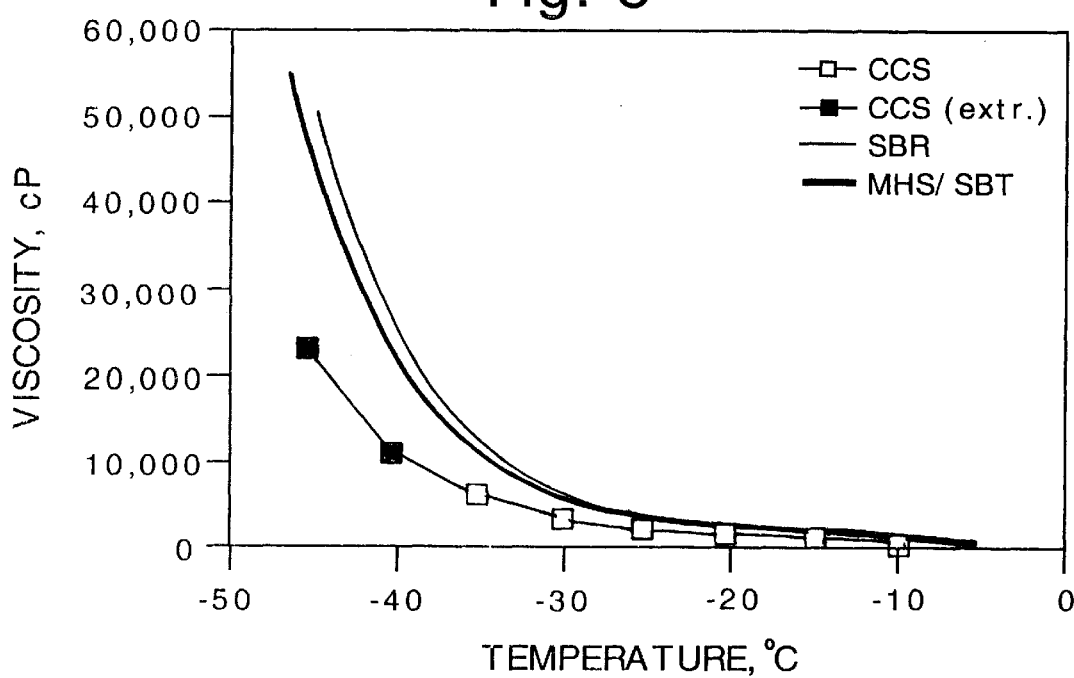

FIG. 8 is a graph showing viscosity-temperature plots at low temperatures using three different instruments of different shear stress (CCS; SBT; and MHS/SBT of SBT-XR) with LTEP-1, a non-gelating oil.

Figure 9:
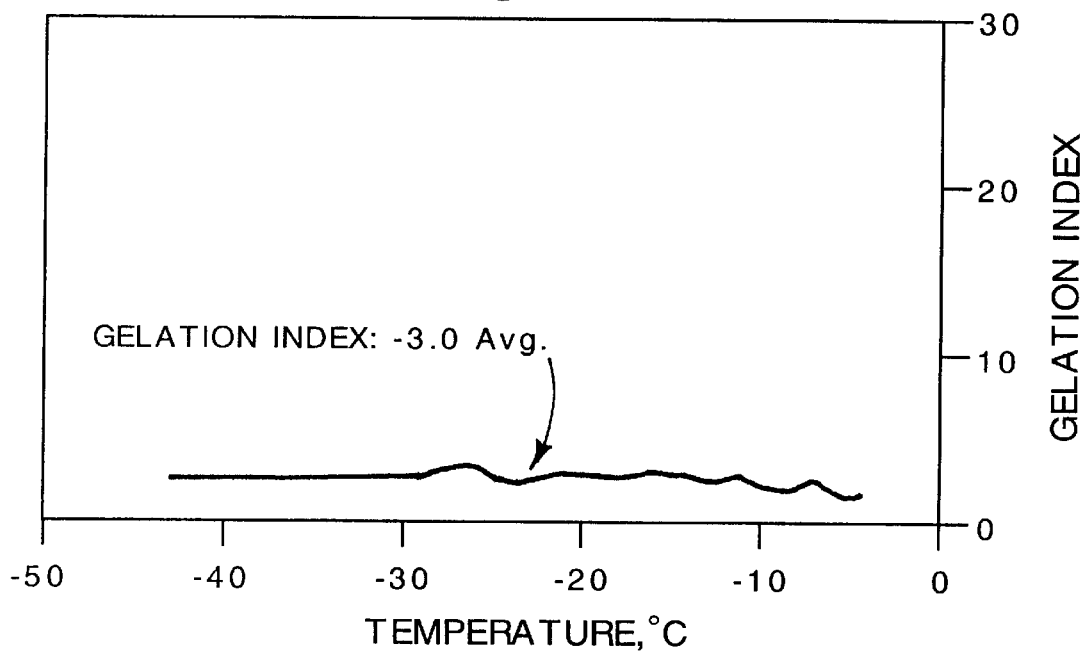

FIG. 9 is a graph showing gelation index of the LTEP-1 oil at moderately high shear stress and a 15-degree C/hr. cooling rate, i.e., MHS/SBT of SBT-XR of the invention.

Figure 10:
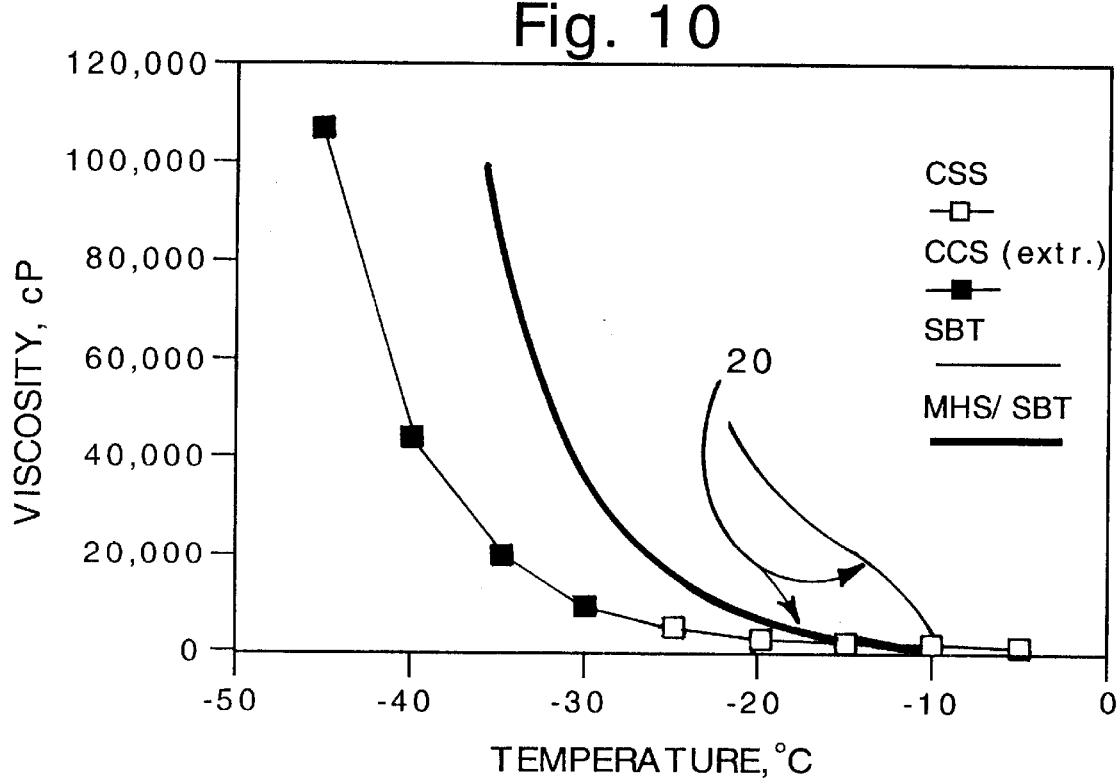

FIG. 10 is a graph showing viscosity-temperature plots at low temperatures using three instruments of different shear stress (CCS; SBT; and MHS/SBT of SBT-XR) with LTEP-26, a gelating oil.

Figure 11:
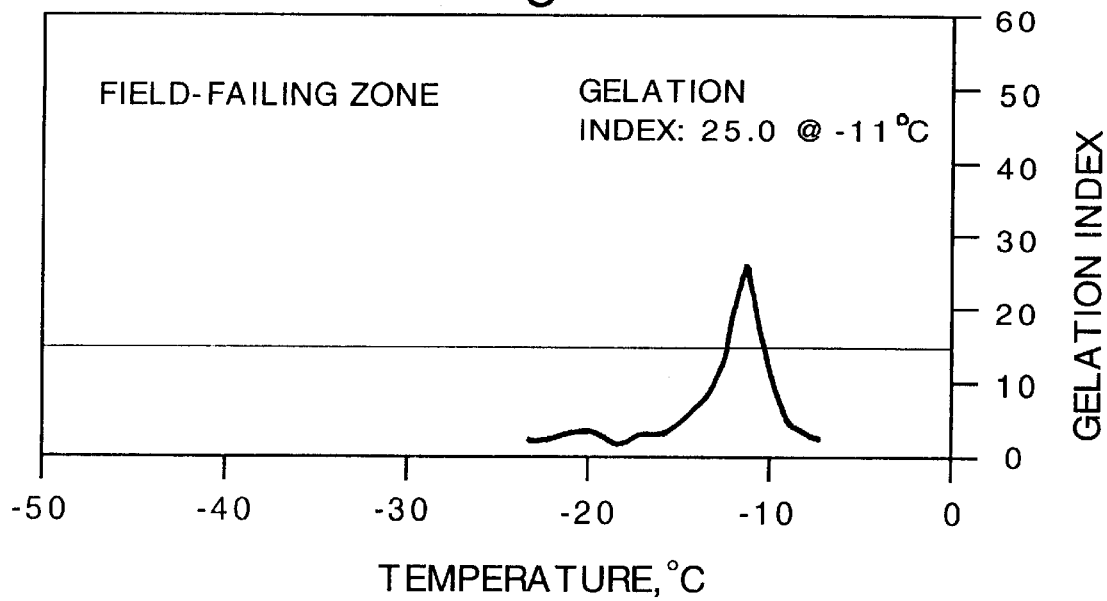

FIG. 11 is a graph showing gelation index and gelation index temperature of the LTEP-26 oil under low shear stress analysis at 1-degree C/hr. cooling rate, i.e., ASTM D 5133 SBT analysis.

Figure 12:
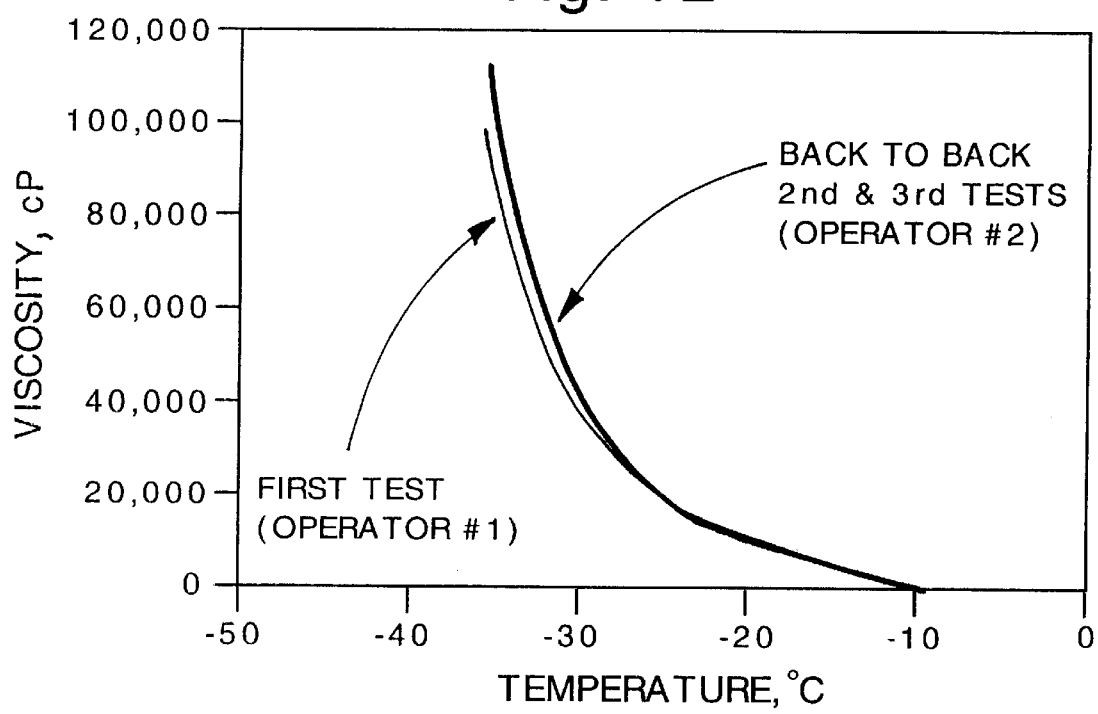

FIG. 12 is a graph showing three viscosity-temperature plots of three individual MHS/SBT analyses of the LTEP oil, with a time period of seven months separating the first and second analyses, done by operators #1 and #2, respectively. This shows the repeatability of the viscosity-temperature curves using MHS/SBT of SBT-XR of the invention.

Figure 13:
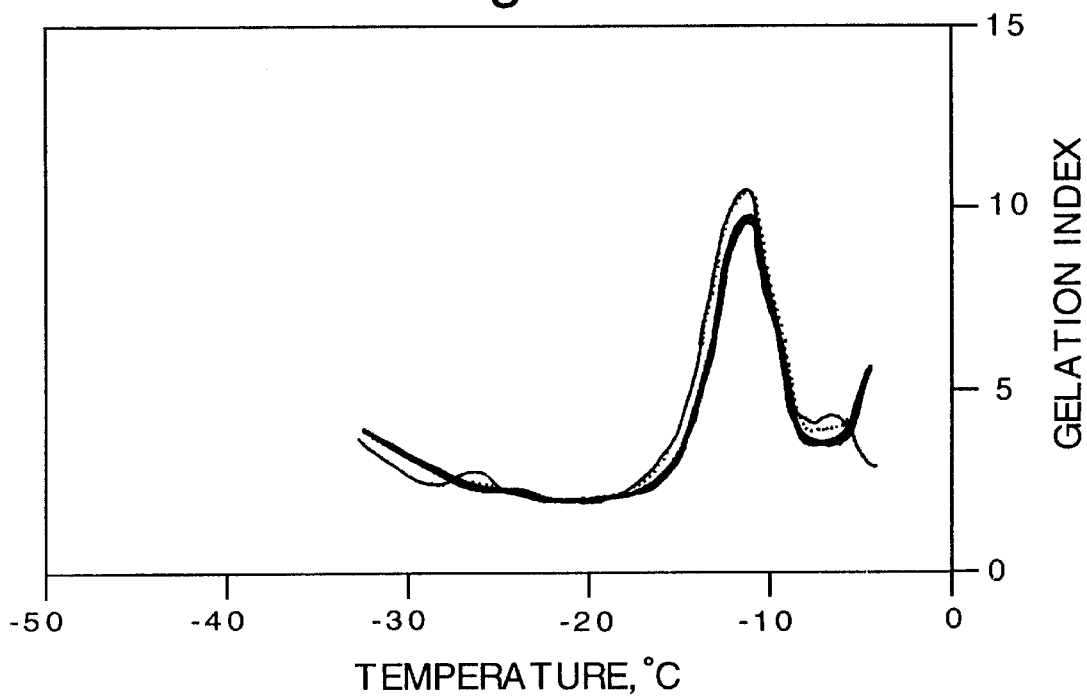

FIG. 13 is a graph showing three gelation index plots of the three individual analyses of the LTEP-26 oil by MHS/SBT from FIG. 12.

Figure 14:
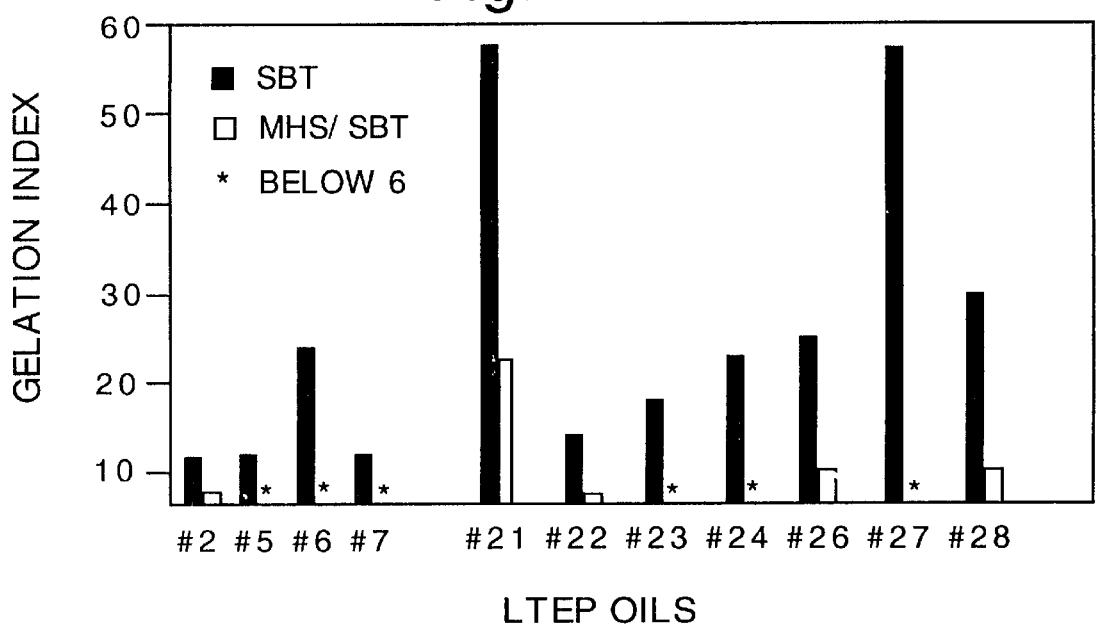

FIG. 14 is a graph showing comparison of gelation indexes of five LTEP oils showing relationship between effects of using SBT (ASTM D 5133) and MHS/SBT methods.

Figure 15:
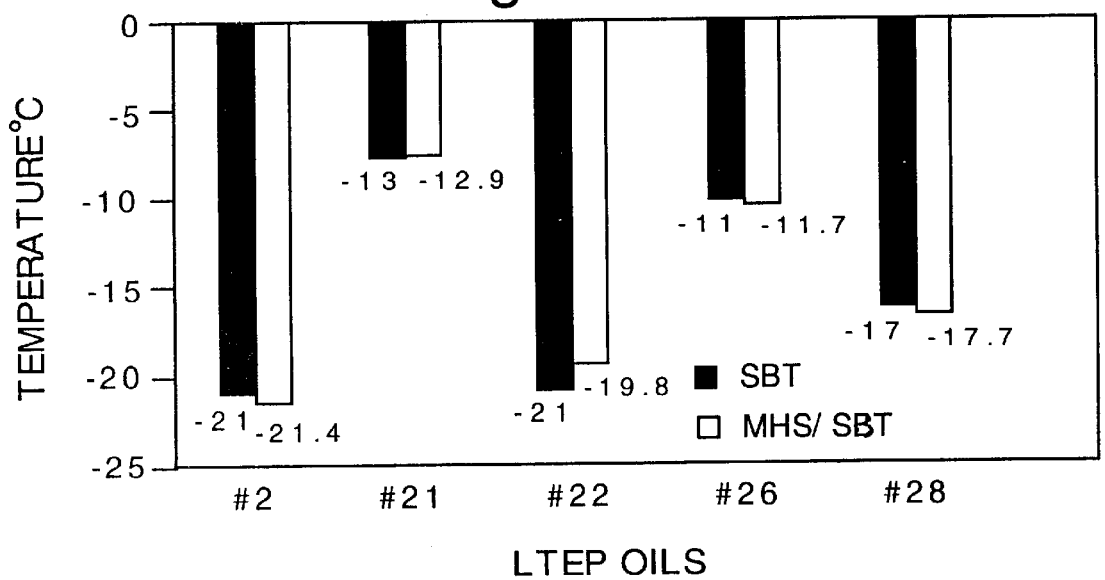

FIG. 15 is a graph showing comparison of gelation index temperatures for five LTEP oils using both SBT (ASTM D 5133) and MHS/SBT methods for analysis.

Figure 16:
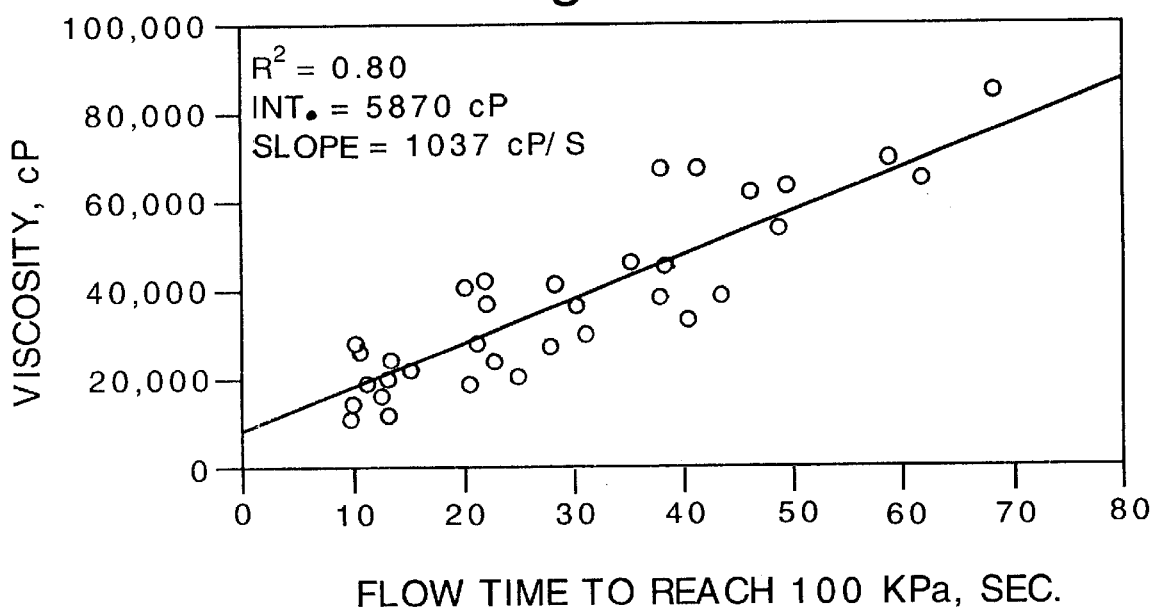

FIG. 16 is a graph showing correlation of pumping data obtained (Laboratory A) at the near galley in an engine (Engine No. 1) using several of the LTEP reference oils. More particularly, correlation of viscosity by MHS/SBT with pump-up time in the near-cam galley is plotted.

Figure 17:
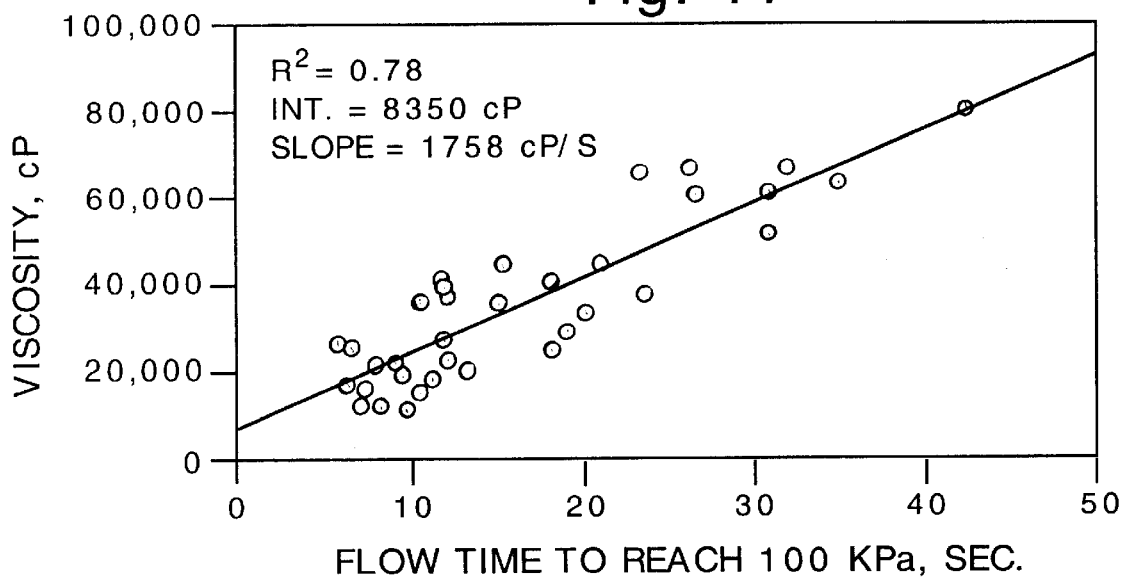

FIG. 17 is a graph showing correlation of pumping data obtained (Laboratory A) at the pump outlet in the engine (Engine No. 1) using several of the LTEP reference oils. More particularly, correlation of viscosity by MHS/SBT with pump-up time at the filter outlet is plotted.

Figure 18:
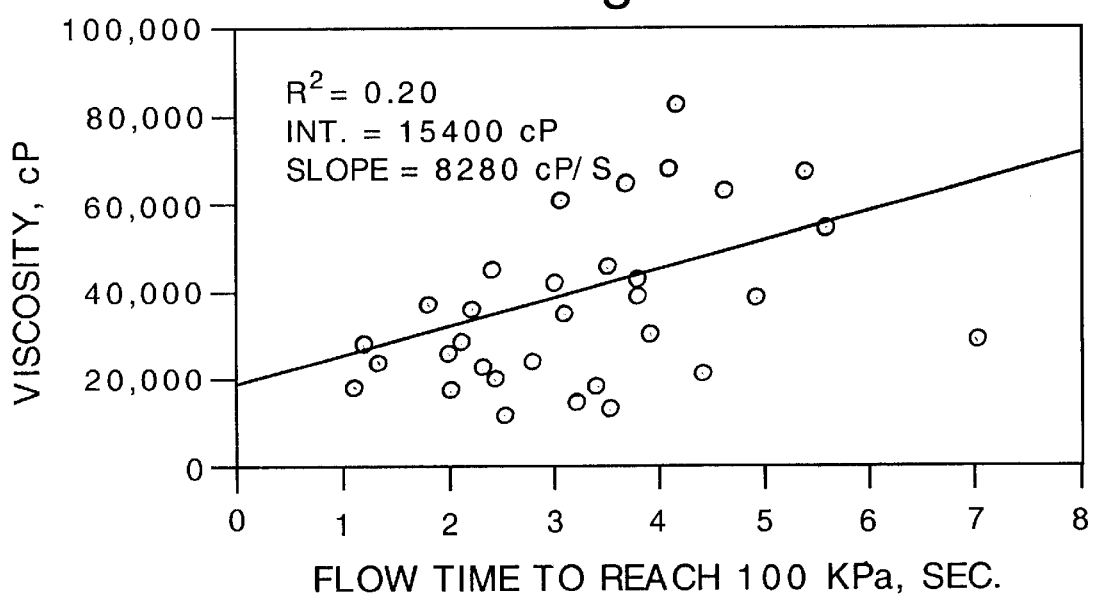

FIG. 18 is a graph showing correlation of pumping data obtained (Laboratory A) at the filter inlet in the engine (Engine No. 1) using several of the LTEP reference oils. More particularly, correlation of viscosity by MHS/SBT with pump-up time in the pump-out line is plotted.

Figure 19:
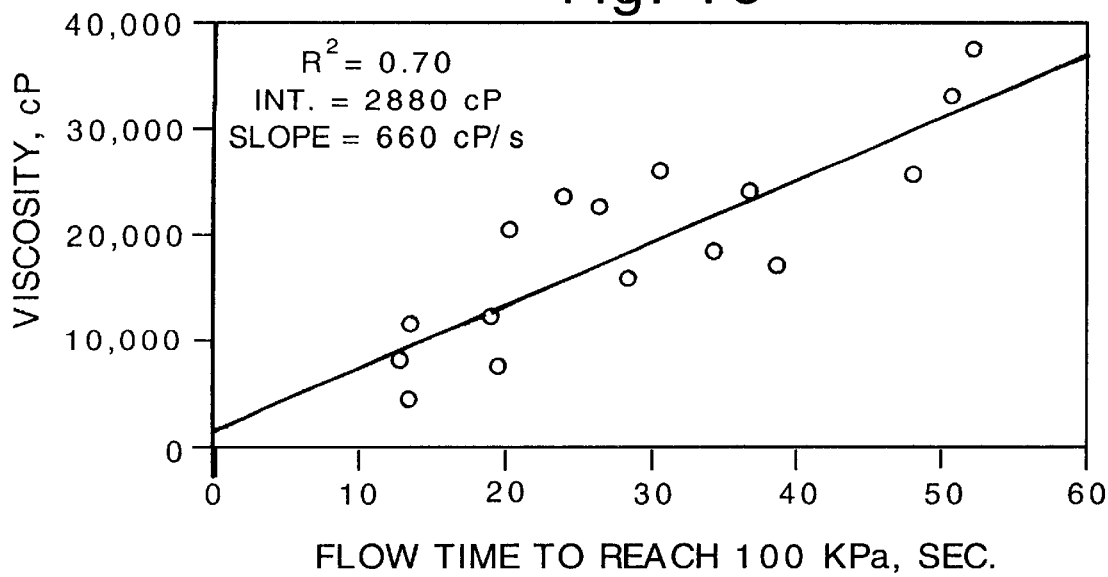

FIG. 19 is a graph showing correlation of pumping data obtained (Laboratory B) at the near galley in an engine (Engine No.2) using several of the LTEP reference oils. More particularly, correlation of viscosity by MHS/SBT with pump-up time in the near galley is plotted.

Figure 20:
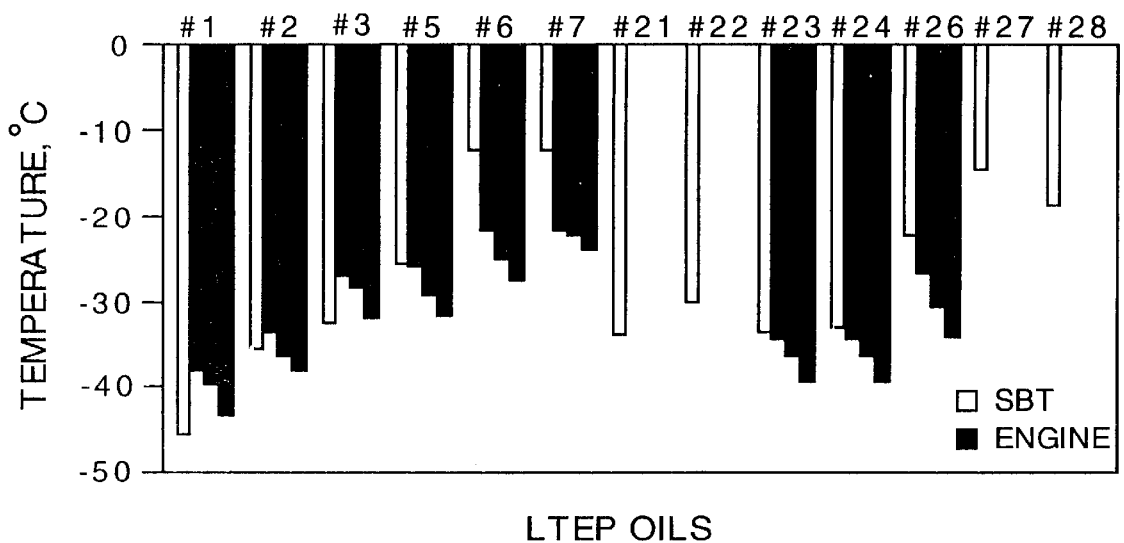

FIG. 20 is a graph, which is a bar chart showing pumping temperatures of engines on LTEP reference oils compared to the lowest temperatures at which SBT reached 40,000 cP. Thus, this is a comparison of minimum SBT temperature to engine pumping temperatures.

Figure 21:
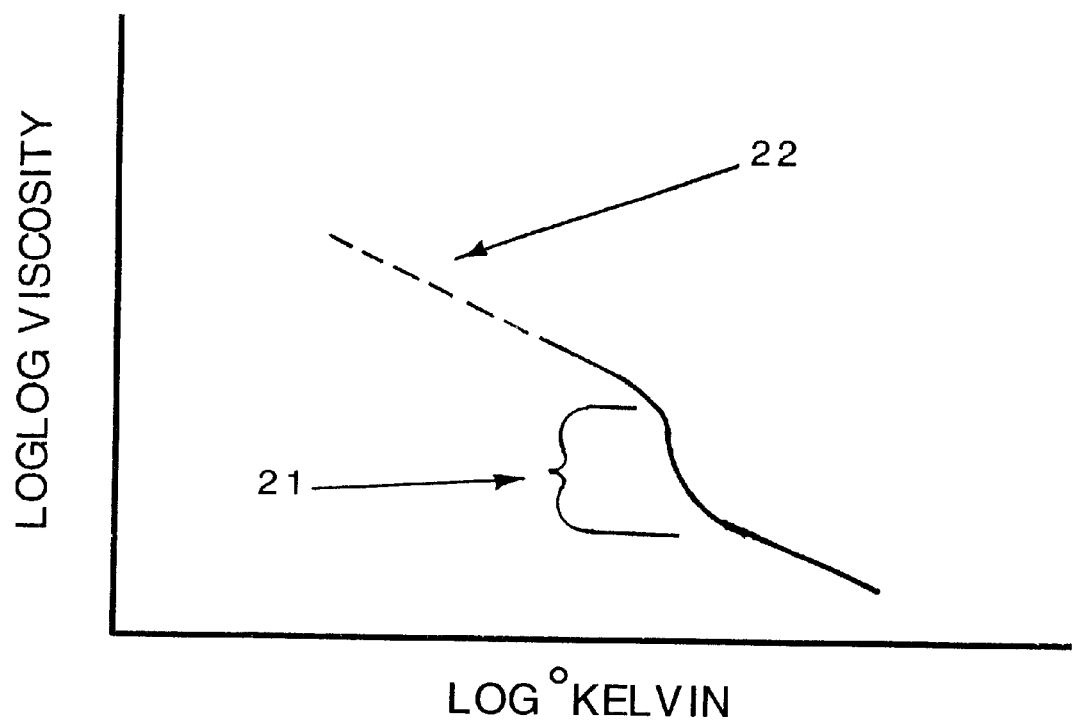

FIG. 21 is a graph showing a method of extrapolating the viscosity-temperature data from some gelated oils. Note, "ogee"-shaped discontinuity 21; extrapolation of final portion of curve 22 (in dashed line).

Figure 22:
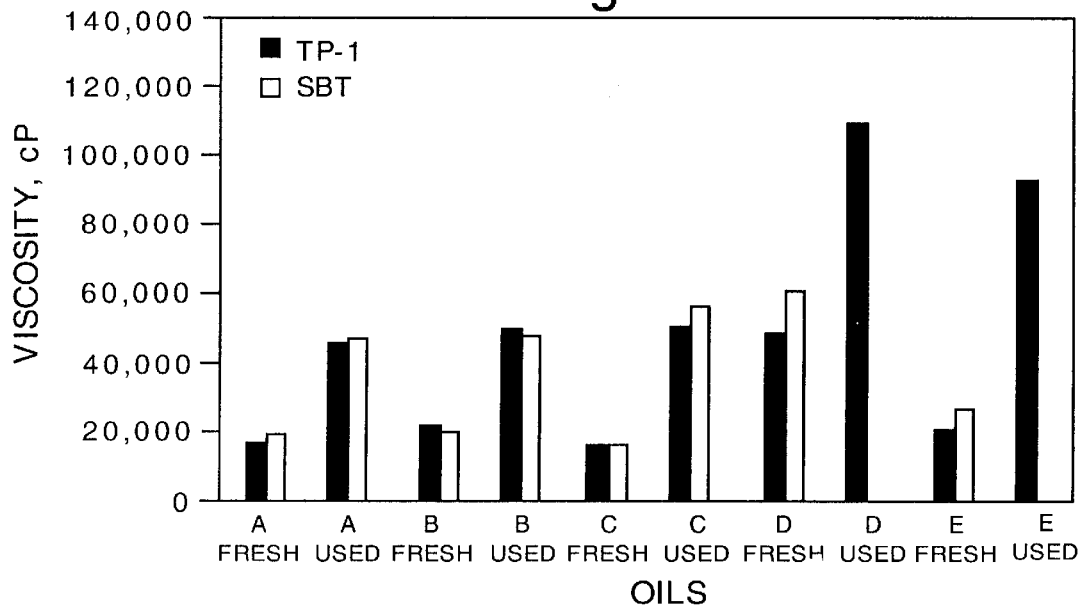

FIG. 22 is a bar graph that plots a comparison of pumpability results of Chevron TP-1 (ASTM D 4684-92) and/or SBT (ASTM D 5133) data for various oils, A–E, both fresh and used. The SBT data was obtained from a standard Scanning Brookfield rotary viscometer having a head with a seventy-Pascal limit to measured torque, at 0.3 revolutions/rotations per minute (rpm) at a temperature drop of one degree C per hour through a range within about from twenty to minus forty-five degrees C. The significance of the FIG. 22 data is that it shows how the normal head cannot respond to data above approximately 50,000 cP whereas the TP-1 technique gives a value.

Figure 23:
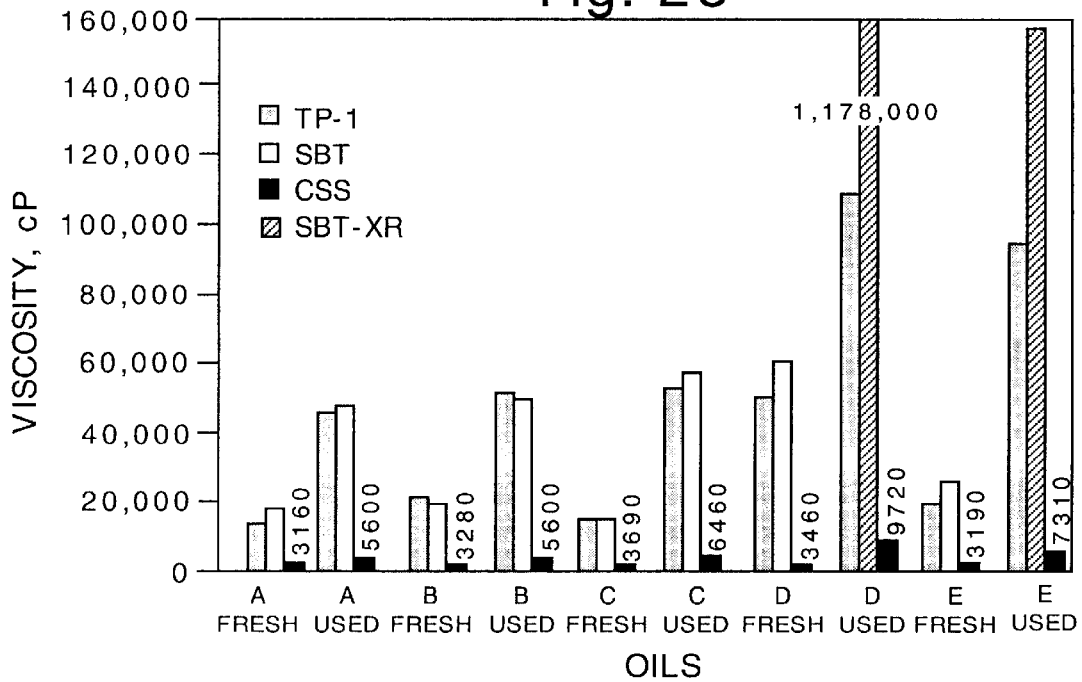

FIG. 23 is a bar graph that plots a comparison of CCS results, and pumpability results from Chevron TP-1, SBT and SBT-XR data for various oils, A–E, both fresh and used. The data includes SBT data, and SBT-XR data obtained from an extended range Scanning Brookfield rotary viscometer with a high torque for oils D & E at conditions otherwise the same or analogous to those employed to obtain the data for FIG. 22. The data illustrated in FIG. 23 shows the benefit of the extended range technology in not only determining the response of highly viscous and gelating oils over the same range as the TP-1 technique but in defining their viscometric properties more clearly. The CCS high shear stress viscometry (ASTM D 5293-98) shows that the rheological properties of the used oils D & E at high shear stresses do not predict low temperature properties found by the data obtained from the high shear stress viscometric approach again using the fresh and used oils A, B, C, D & E. The significance of FIG. 23 especially in comparison to FIG. 22 is that the comparison shows the benefit of obtaining data with the higher shear stress technique. The data obtained with the high torque head containing temperature-scanning rotary viscometer was obtained with a shear stress of over one thousand Pa.

Figure 24:
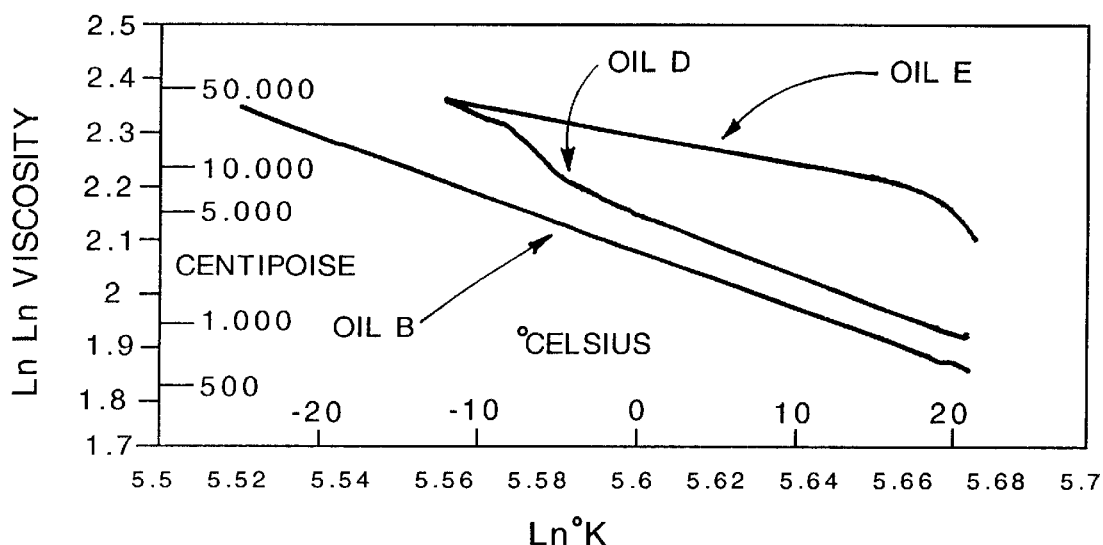

FIG. 24 shows MacCoull, Wather, Wright plots showing different soot-handling abilities of three heavy-duty engine oils, B, D & E, each of which has been plotted from data taken on the dirty sample from the respective pair. The significance of the FIG. 24 data is that the figure shows the considerable rheological differences among the three oils, B, D & E, using the normal scanning rotary viscometric procedure. Even so, the data terminate at about 50,000 cP—the limit of the torque spring of the head. Oils D & E show essentially equivalent viscosities at this point but appear to be trending differently. This figure also shows the normal Newtonian Behavior of oil B when contrasted to the behavior of oil D, which shows gelated behavior accompanying the high soot loading, and oil E, which shows strong soot-induced rheology associated with soot-agglomeration.

Figure 25:
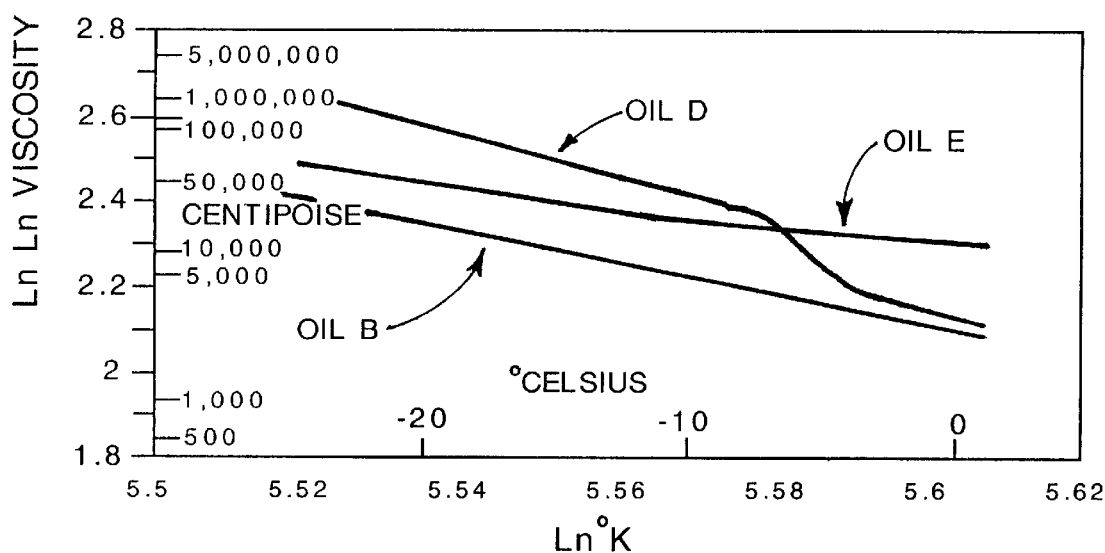

FIG. 25 shows MacCoull, Wather, Wright plots showing different soot-handling abilities of three heavy-duty engine oils, B, D & E. The FIG. 25 data shows the full analyses of the three dirty oils of FIG. 24 when the much higher stress temperature-scanning rotary viscometry, i.e., MHS/SBT, of the present invention is applied. The trends of the oils D & E have been made fully clear, and it is evident that there is considerable difference in their viscosities at minus twenty degrees C. It is also evident that the gelating tendency of oil D is not lost by using the higher torque head and rheological technique of the invention.

Figure 26:
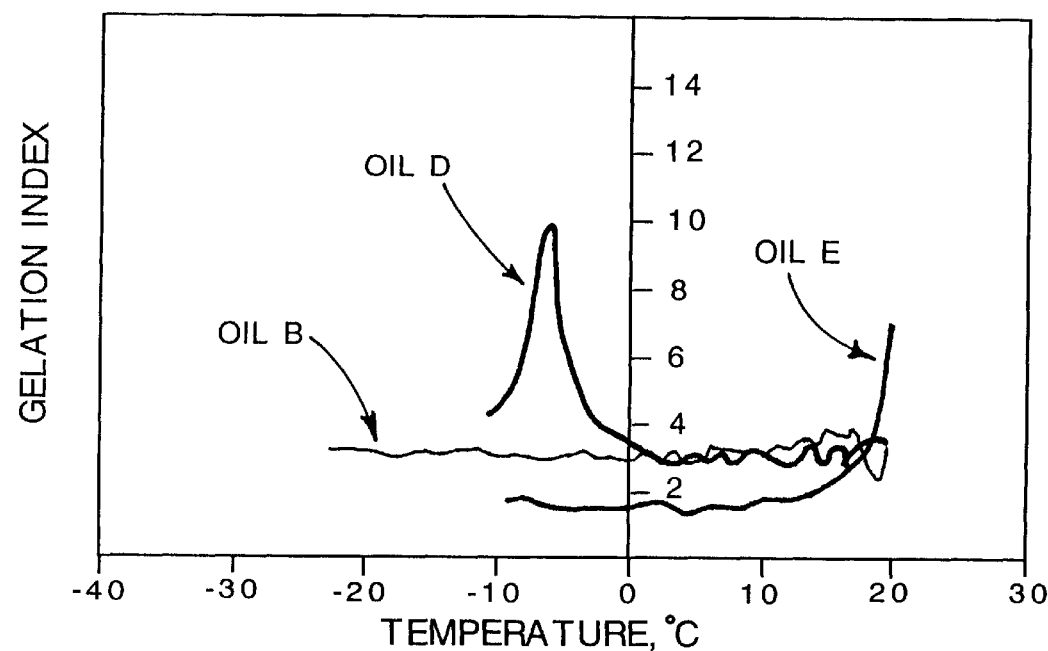

FIG. 26 shows gelation index curves of three highly sooted engine oils, B, D & E. The FIG. 26 data shows the gelation curves for the dirty oils B, D & E which were calculated from the data of FIG. 24 using the normal viscometric head technique, i.e., SBT. An evident gelation index peak is shown for oil D. Since the viscosity of oil B is much lower, the gelation index line is able to be determined down to lower temperatures.

Figure 27:
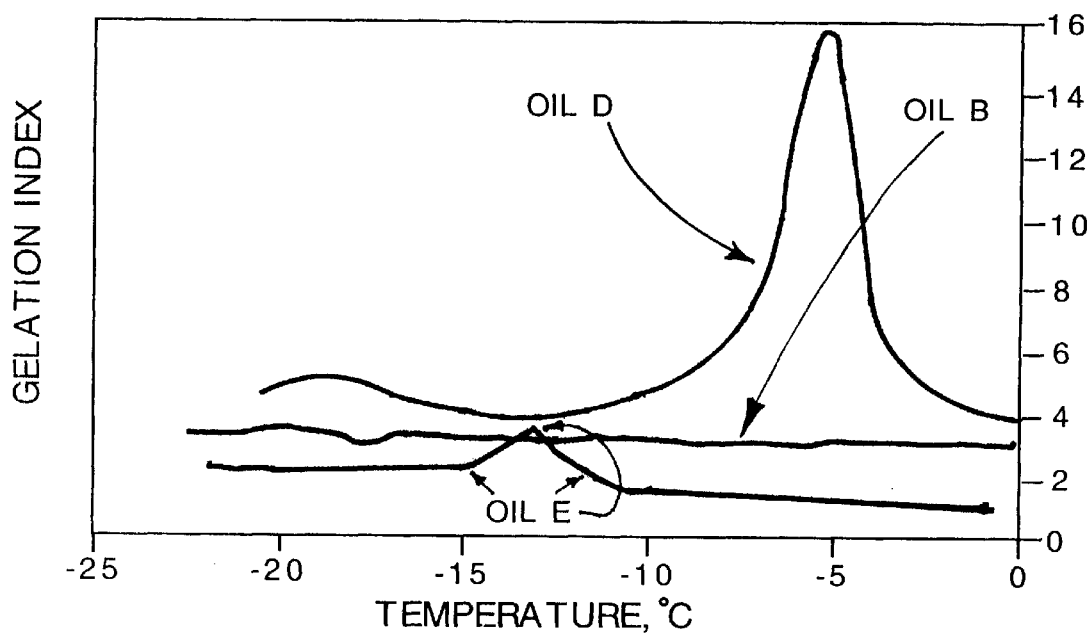

FIG. 27 shows gelation index curves of three highly sooted engine oils, B, D & E, each of which has been plotted as the dirty sample from the respective pair with data of FIG. 25 using the high stress viscometric head technique, i.e., MHS/SBT or SBT-XR of the invention. Interestingly, the sensitivity of the technique to the presence of gelation is even greater with this high stress approach, which employs a high torque spring in the otherwise well. known rotary viscometric head than with employment of the normal torque spring, as shown by the gelation index peak for oil D. The normal technique gave a gelation index peak of about ten while the new technique and equipment gave a gelation index value of about 15.5. This was unexpected and a strong indication that the new technique and equipment has greater applicability than the previous rheological approach. This is one of the greatest advantages of the new approach in that the viscosity range capable of being covered is many times greater than that approach which employs the normal or standard rotating viscometer head. In addition, the data gathered and shown in FIG. 27 has considerably greater temperature range than that in FIG. 26 owing to the fact that much higher viscosity materials can be measured effectively, and a second, smaller gelation index peak begins to show at minus nineteen degrees C. This peak could not have been revealed by the normal approach, the data from which was employed to provide FIG. 26, because of the limited viscosity range. Oil E also shows a small peak at minus thirteen degrees C which could not be revealed by the normal technique.

Also with respect to FIGS. 22–27, FIGS. 22 & 23 show data graphed with respect to oils A & C, the data of which do not appear in FIGS. 24–27. Oils A & C are well behaved oils like oil B, and, of course, only one oil is necessary to show the contrast with oils D & E. The oil selected to show the contrast is oil B.

Figure 28A:
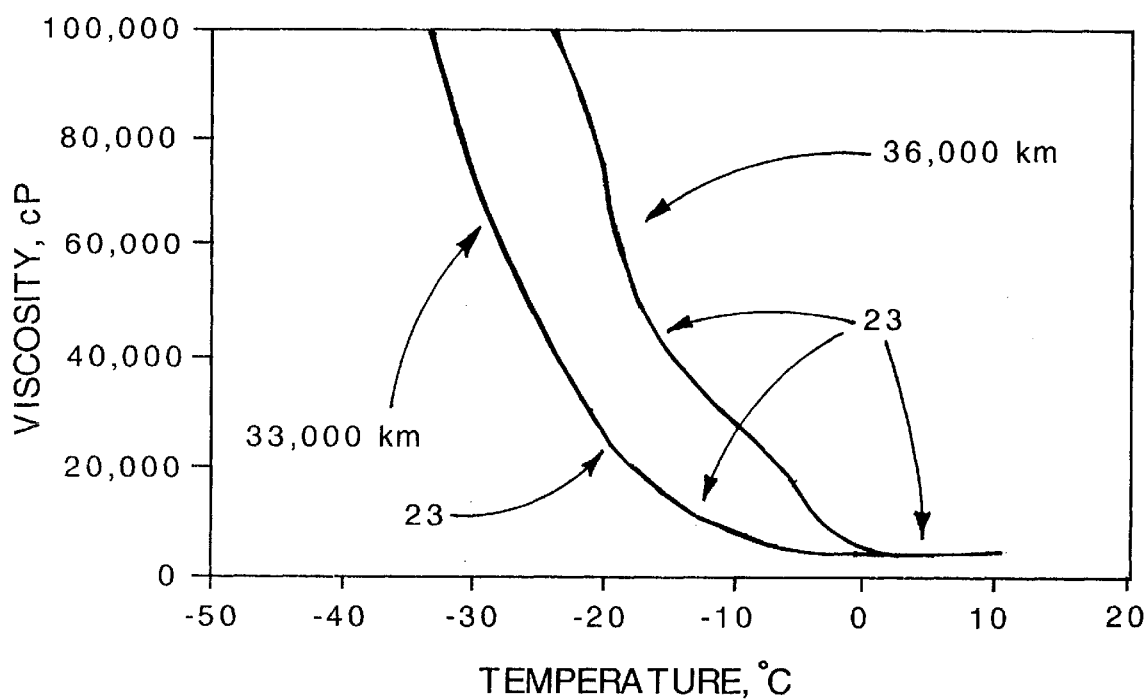
Figure 28B:
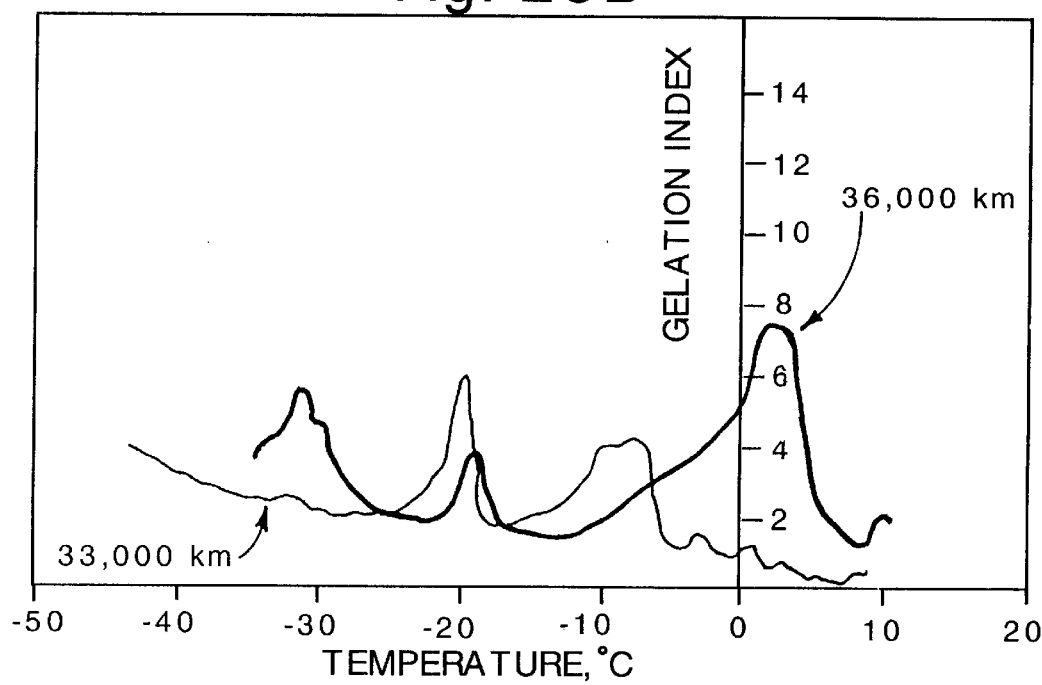

FIG. 28 consists of two drawings, FIGS. 28A & 28B. FIG. 28A is a graph showing viscosity-temperature curves of two samples of 5W30 engine oil taken from a lease car at 33,000 and 36,000 km of driving, representing SBT results on highly oxidized oil samples, with initiation of gelation points 23 identified; and FIG. 28B is a graph showing gelation index curves of the two samples of oil from FIG. 28A.

Figure 29:
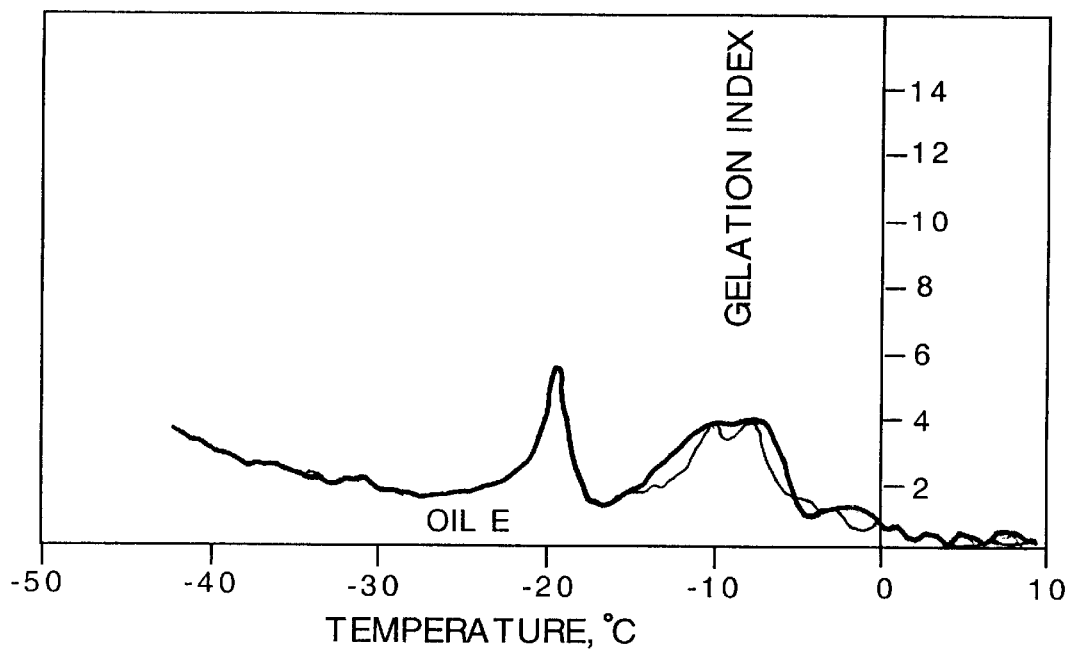

FIG. 29 is a graph showing repeatability of the gelation index curves using two samples of the 30,000-km test oil from FIGS. 28A and 28B.

Figure 30A:
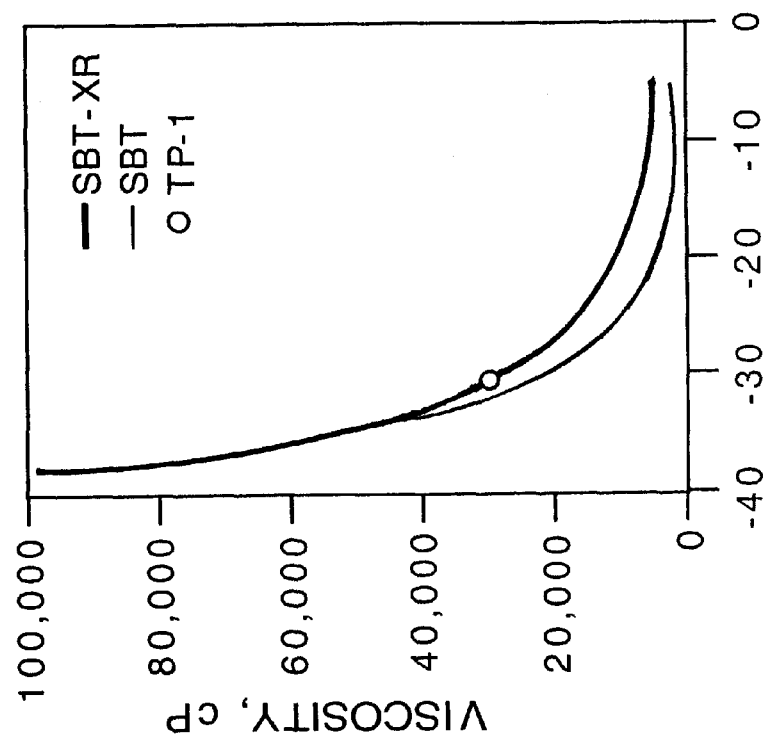
Figure 30B:
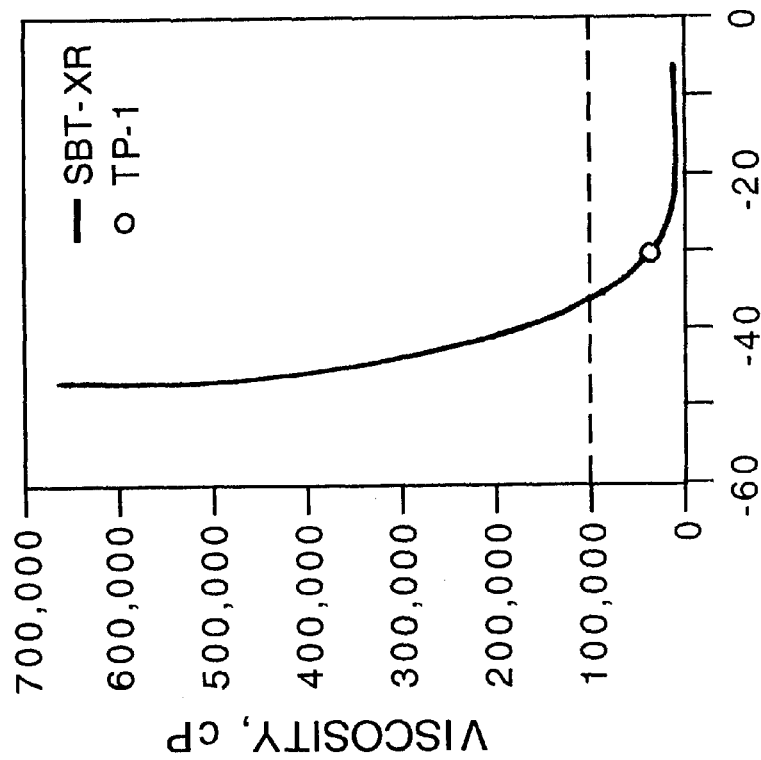

FIG. 30 consists of three drawings, FIGS. 30A, 30B & 30C. These are graphs showing an extended viscosity-temperature curve for a 10W40 engine oil (oil K) (FIG. 30A); a section of the viscosity-temperature curve from FIG. 30A (FIG. 30B); and the gelation tendency of the oil K (FIG. 30C). This information is presented with the permission of IOM, Inc.

Figure 1:
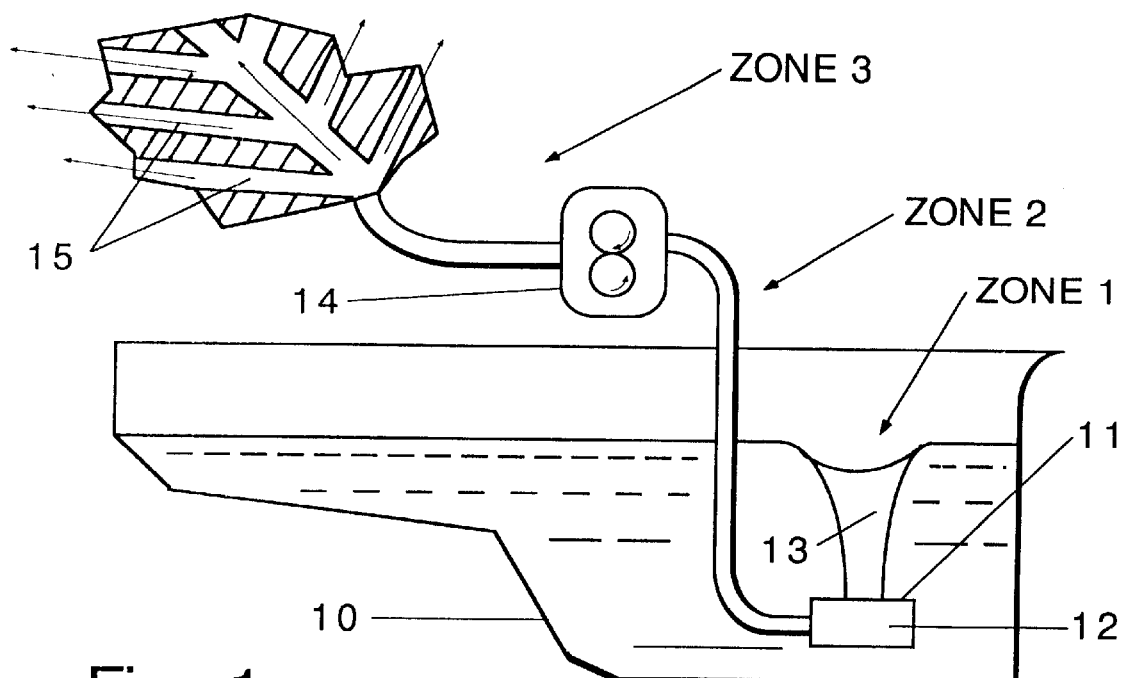
Figure 31C:
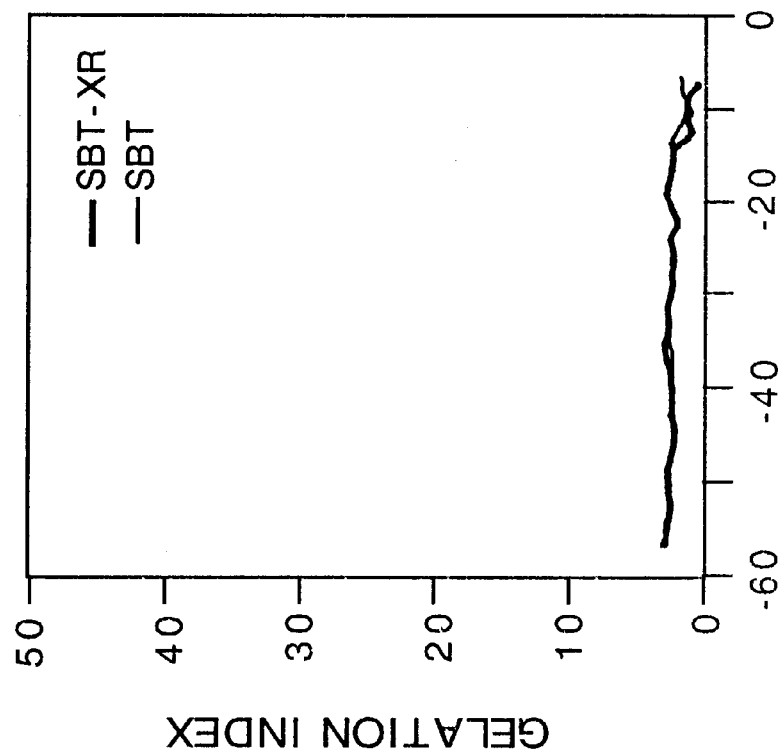
Figure 31B:
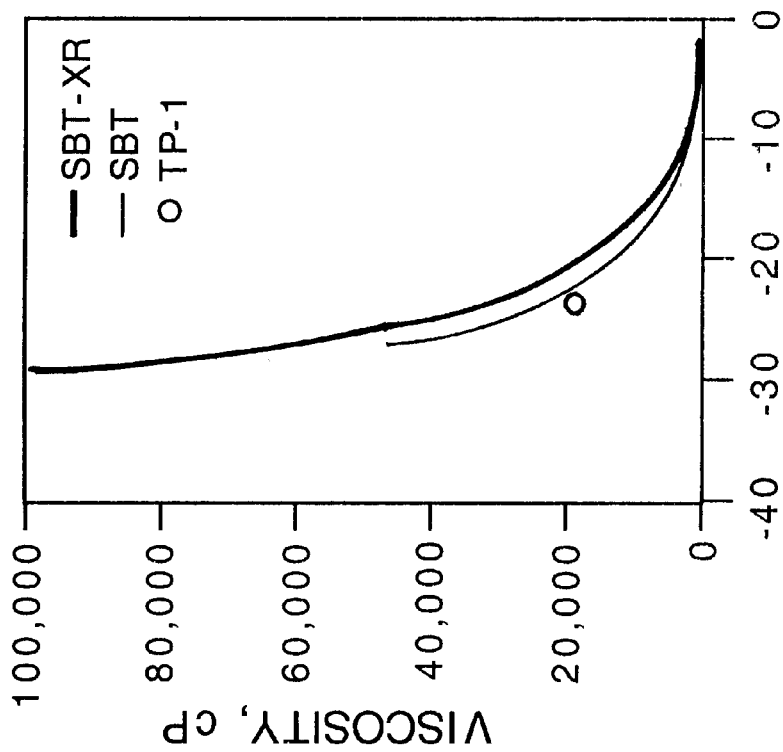

FIG. 31 consists of three drawings, FIGS. 31A, 31B & 31C. These graphs showing an extended viscosity-temperature curve for a 5W50 engine oil (oil G) (FIG. 31A); a section of the viscosity-temperature curve from FIG. 3 1A (FIG. 31B); and the gelation tendency of the oil G (FIG. 31C). This information is presented with the permission of IOM, Inc.

Figure 32A:
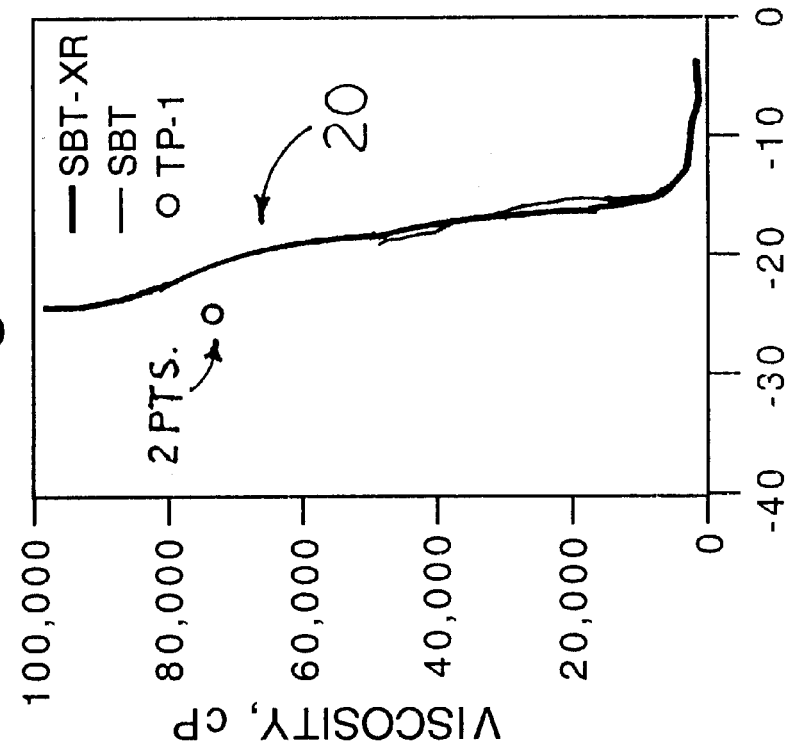
Figure 32B:
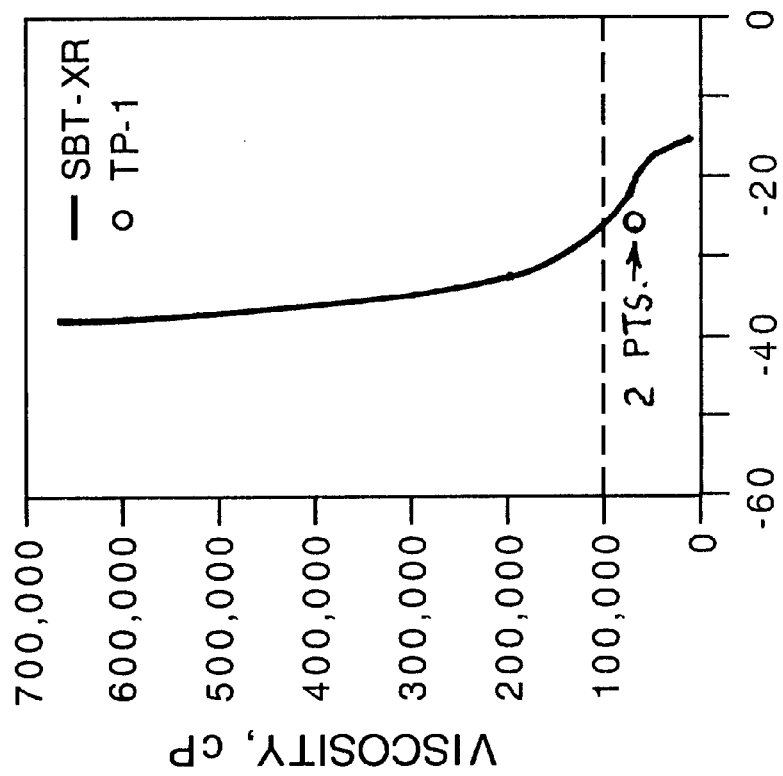

FIG. 32 consists of three drawings, FIGS. 32A, 32B & 32C. These are graphs showing an extended viscosity-temperature curve for a 15W40 engine oil (oil A) (FIG. 32A); a section of the viscosity temperature curve from FIG. 32A (FIG. 32B); and the gelation tendency of the oil A (FIG. 32C). This information is presented with the permission of IOM, Inc.

Figure 33C:
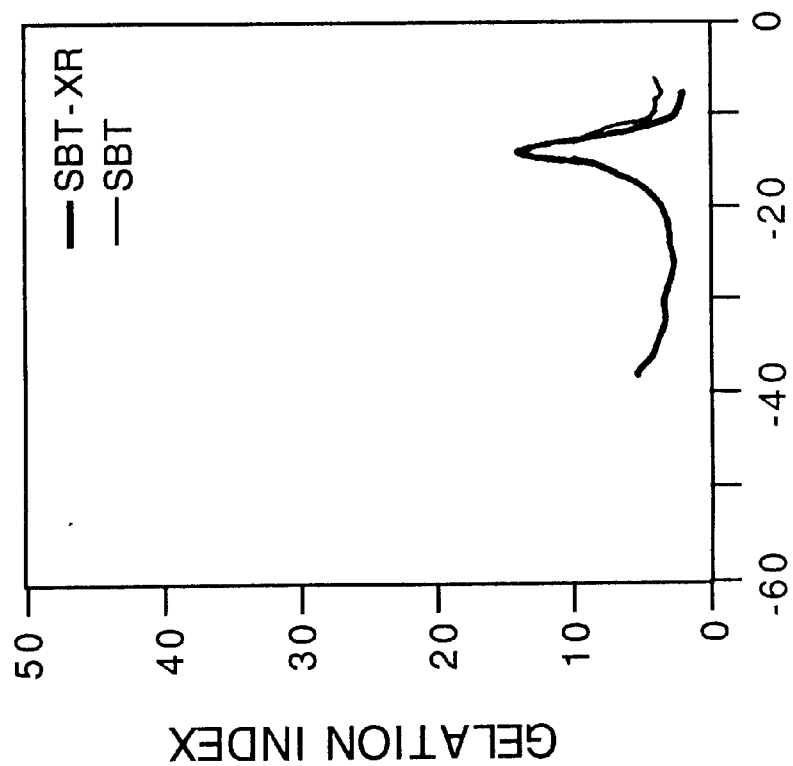
Figure 33B:
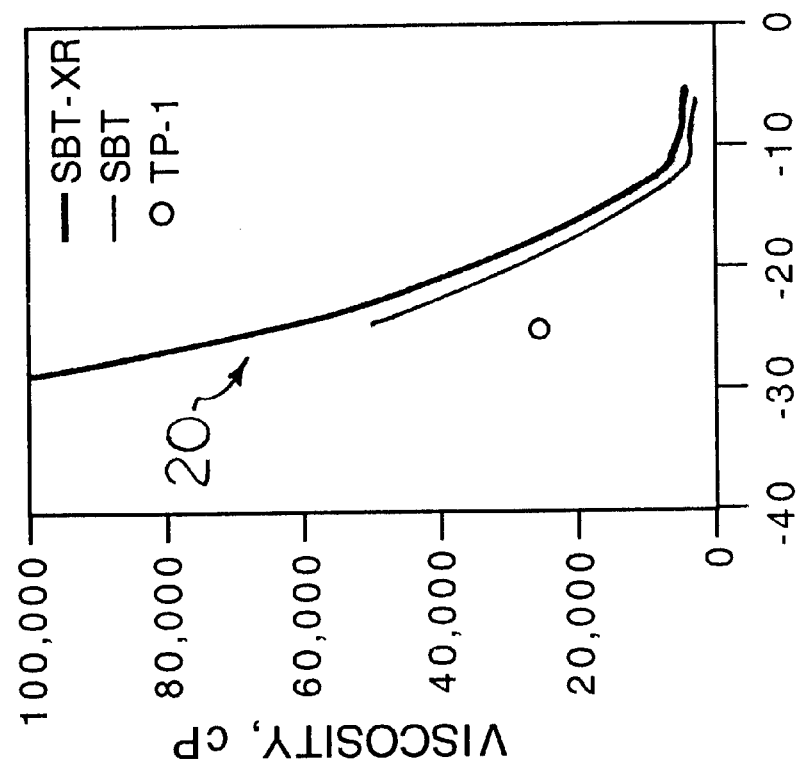

FIG. 33 consists of three drawings, FIGS. 33A, 33B & 33C. These are graphs showing an extended viscosity-temperature curve for a 15W40 engine oil (oil D) (FIG. 33A); a section of the viscosity temperature curve from FIG. 33A (FIG. 33B); and the gelation tendency of the oil D (FIG. 33C). This information is presented with the permission of IOM, Inc.

Figure 34B:
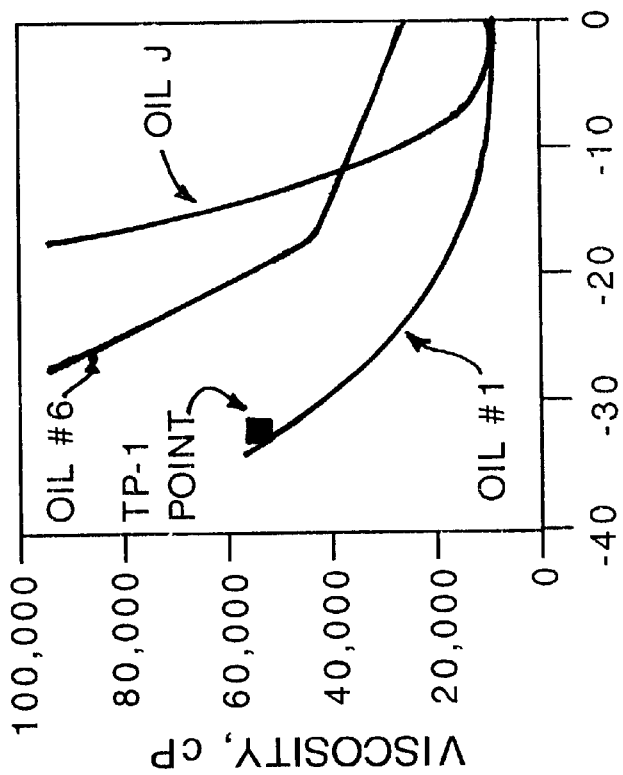
Figure 34A:
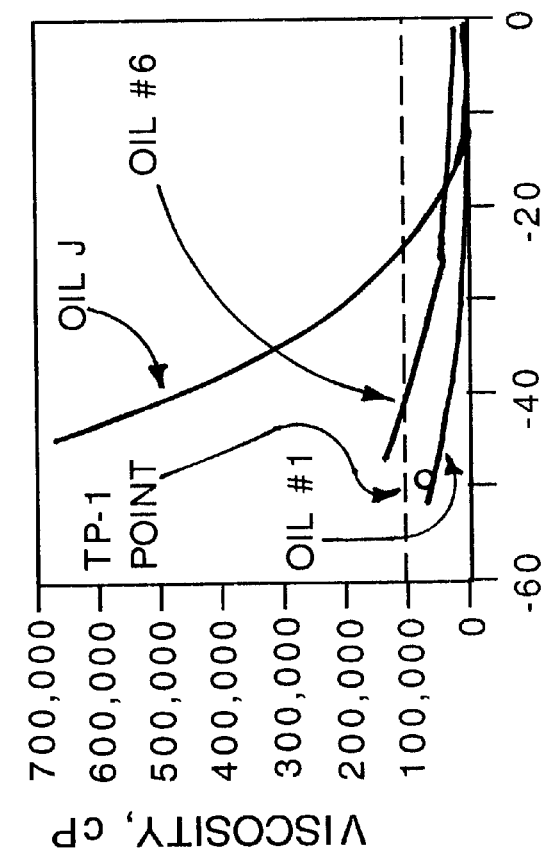

FIG. 34 consists of three drawings, FIGS. 34A, 34B & 34C. These are graphs showing SBT-XR comparisons, i.e., extended viscosity-temperature curves, for highly sooted, 15W40 heavy duty engine oils (FIG. 34A); a section of the viscosity-temperature curve from FIG. 34A (FIG. 34B); and the gelation tendency of the oils (FIG. 34C).

Figure 35:
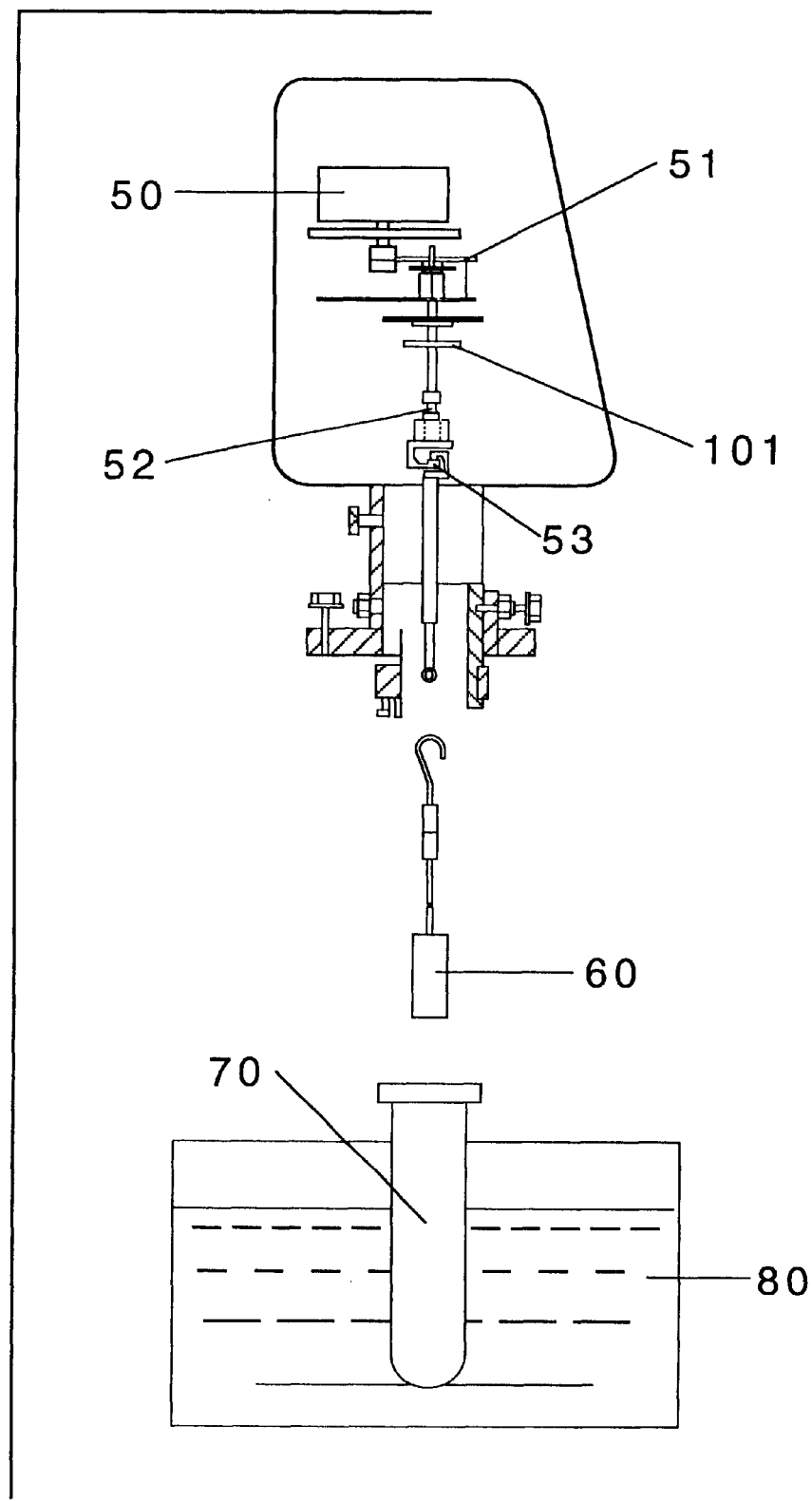

FIG. 35 is an exploded, plan view of a high torque Brookfield rotational viscometer head employed in the practice of the invention.

ILLUSTRATIVE EXPOSITION OF THE
INVENTION THROUGH FURTHER DETAIL
AND REFERENCES TO ADDITIONAL ART

The invention can be further understood by the present detail, which may be read in view of the drawings. The same should be taken, as well as should be the foregoing, in an illustrative and not necessarily limiting sense.

Reference to MHS/SBT or SBT-XR is directed to the present invention. The terms may be used interchangeably. However, MHS/SBT is included within SBT-XR, but SBT-XR is not necessarily encompassed entirely by MHS/SBT. In other words, SBT-XR is the broader term.

In general, in the practice of the present invention, in a rotating viscometer technique, which preferably is an SBT, the improvement can include provision of a higher torque head with a torque substantially greater than about seventy Pa, which may be considered to be a torque substantially greater than that provided by the normal head. Preferably, the substantially greater torque is at least about ninety Pa, and, more preferably, about one thousand Pa or more, as long as sensitivity to gelation is retained. Minimum torque values intermediate to the foregoing numerical values can be employed, to include at least about one hundred fifteen, two hundred thirty, and five hundred eighty Pa, and above, say, about one thousand one hundred fifteen Pa, or more.

Thus, in general, the method of the invention is useful for testing a fluid in high shear stress viscometry. In contrast to low shear stress viscometry, where viscosities are encountered which typically range in about the 10 cP range, which is useful with respect to determining characteristics of fuels, and so forth, high shear stress viscometry can encounter viscosities in about the 1000-poise (P) range, or even higher. For example, the temperature-scanning, rotational viscometry of the invention may encounter viscosities in the 2000-P, 3000-P, 4000-P, 5000-P or even 10,000-P range, or higher. In other words, high shear stress viscometry can employ stresses up to five to fifty orders of magnitude, or greater, more than low shear stress viscometry.

In the practice of the method of the invention, a number of steps can be carried out. The steps may be carried out in series as described or out of that series, or plurality of steps may be carried out simultaneously as, for example, with respect to data collection.

A test fluid is provided. Preferably, the test fluid is a liquid. Preferably, the liquid is a lubricant. Liquid lubricants may include engine oils, gear oils, automatic transmission fluids, and so forth. The invention is particularly well-adapted for testing engine oil samples.

A temperature-scanning Brookfield-type viscometer is provided as the test instrument. Suitable Brookfield-type viscometers and components are well-known in the art. For example, they are commercially available from Tannas Co., Midland, Mich., and patents and/or other references which describe these may be found. In general, the temperature-scanning Brookfield-type viscometer is a rotary instrument, which, as depicted in FIG. 35, includes a motor, e.g., synchronous motor 50, which drives rotor 60 through gear train 51, pivot shaft 52, and jeweled bearing 53; stator 70 in which the test fluid is to be contained, and temperature-control feature 80. The rotor 60 is immersed and driven in the test fluid in the stator 70, and the temperature-control feature 80 controls the temperature of the test fluid during testing. The temperature-control feature 80 can be provided by a gas or liquid bath, preferably the liquid bath, for example, a cold methanol bath, the temperature of which is controlled with a high degree of accuracy and precision. Thereby, low-temperature testing can be accomplished. See, e.g., Selby et al., U.S. Pat. No. 5,503,002, incorporated herein by reference. Typically, Brookfield-type viscometer instruments are available in a variety of head (motor-containing) sensitivities: LV (low); RV (medium); HV (high); HB (very high). Note, TABLE 1:

TABLE 1

| Head Sensitivities | |
| --- | --- |
| Head Type | Spring Stress |
| LV | 673.7 dynes/cm sq |
| RV | 7187 dynes/cm sq |
| HV | 14374 dynes/cm sq |
| HB | 57496 dynes/cm sq |

Preferably, in the practice of the invention, the temperature-scanning Brookfield-type viscometer is outfitted with a stronger head, e.g., the HV head. Beneficially, the temperature-scanning Brookfield-type rotational viscometer may be outfitted with an even stronger head than the HV head, for example, a head which can provide for measurement of twenty-five or fifty percent greater torque, or twice or thrice the torque as the HV head, which known head generally can measure a torque of some four thousand Pa. Thus, heads of the invention can have a torque substantially greater than four thousand Pa such as of five, six, eight or twelve thousand Pa. Nonetheless, the Brookfield-type head can have the at least about 90-Pa torque to be considered substantially greater than a normal torque of about 70 Pa, and be in the preferred practice of the invention. A torque of about 1,000 Pa or more can be provided the head, as previously mentioned.

The test fluid is provided to the stator in an amount suitable to the configuration and volume of the stator, and the rotor. For example, with a typical 22-millimeter (mm) diameter glass stator and 65.5-mm long by 18.42-mm diameter stainless steel rotor, an approximately 20-milliliter (mL) sample of engine oil as the test fluid can be poured into the stator. The rotor is immersed in the test fluid in the stator, with the typical set-up of the temperature-scanning Brookfield-type viscometer generally being conducted.

During the testing, the rotor immersed in the test fluid is driven by the motor of the Brookfield-type viscometer under high shear stress conditions. While this is being carried out, the temperature of the temperature-control feature, and hence, the test fluid, is varied as a function of time over a suitable period of time. This can be generally about half a day or less, preferably about eight hours or less, more preferably about six hours or less, and most preferably about two or three to four or so hours, or less. In particular, in a preferred embodiment, the new temperature-scanning bench test operating at the higher shear stresses and completing an analysis from −5 to −50 degrees C in three hours, has shown good correlation with ASTM LTEP cold-room pumpability data. The speed of analysis of the new method of the present invention also provides for quality control for engine oils formulated to be gelation free. During this time, the temperature is lowered from and to a suitably low value, which can depend on the test fluid, the rotor and stator selected, and the actual shear stress encountered. As examples of this, temperature can be varied from about zero degrees C, to about minus fifty or sixty degrees C, in a sort of hyperbolic manner over several hours; or, say, as in the case of an engine oil as the test fluid, the temperature can be varied from minus five degrees C to minus forty degrees C, with a linear temperature drop of fifteen degrees C per hour. Rotation of the rotor within the stator is conducted at any suitable speed. A rotation rate selected from about from 0.1 or 0.2 to five or ten rpm may be employed. For example, a 0.3-rpm rate has been effectively employed. A 3-rpm rate may be employed.

During the testing, monitoring the stress and/or viscosity of the test fluid is carried out, and data is obtained therefrom. A typical arrangement employs electronic sensing of the drag on the rotating rotor, which is communicated to a display terminal. The use of computer monitoring and incremental iteration such as by a suitable algorithm which may employ differentiation from above and below a target value so as to in effect reduce or eliminate noise is advantageously carried out.

Unique to the invention, in particular with respect to the testing of engine or motor oils, are its employment of high stress; its relatively short run times, and yet, the scanning of the temperature range while the rotational viscometry is being conducted to obtain a whole range of information under such conditions of high stress and relatively rapid temperature change into lower temperature regions. Obtained thus include such data as that useful to determine the viscosity at various low temperatures, the tendency toward and degree of gelation, and the temperature at which gelation forms.

The high levels of torque can be provided by providing a more stiff spring, e.g., calibrated spiral spring 101, within the otherwise well known rotating viscometer head for measuring increased drag or torque of the rotor immersed in the sample in the stator. See, FIG. 35. Of course, the Scanning Brookfield viscometer includes such a rotating viscometer head, the structural detail of which is well known in the art. In the practice of the invention, moreover, the sample is subject to a temperature variation, typically as a lowering of the temperature of the sample in the stator which is immersed in a cooling bath at a certain linear rate. Temperature variations need not, however, be linear, nor is it necessarily desired that the temperature be lowered through a range since an increasing, oscillating, or stepped value of temperature may be employed as an alternative in the practice of the invention.

In turn, liquid samples having viscosities as high as about 800,000 cP or greater such as a million cP, two million cP, three million cP or so may be effectively characterized. What is more, refinements in elicitation of data, heretofore uncollectable or uncollected, related to development of structural characteristics of a sample as it changes from a liquid into a sample having gel and/or crystal or the like properties can be collected. Along these lines, of course, as the speed of rotation increases, so can the sensitivity, with a corresponding decrease, however, in the range of measurement. Thus, for example, with an HV head with a 4000 Pa torque, a test liquid with an 800-P viscosity can be measured at a 0.2 shear rate.

Pumpability studies may be conducted in conjunction herewith.

Higher shear stress low temperature engine rheology is further described below

Low-temperature oil flow in the engine is of importance.

The length of time for the oil to develop pressure at various locations in the engine after flow from the pump through the galleys is obviously the final criterion for acceptable pumpability regardless of whether the cause is air-binding (gelation-induced flow condition) or flow-limited behavior (viscosity-induced flow condition).

Instrument correlation is of concern. If an oil is found to be strongly gelated in a bench test correlating with past field results and yet the oil or engine is not showing effects of gelation in the cold-room, then instruments which are gelation-sensitive would not be expected to correlate well with the engine pumpability data. For example, the SBT test method (ASTM D 5133) would show inappropriately high viscosities caused by oil gelation. The MRV/TP-1 test method (ASTM D 4684) also responds to gelation. Although the method requires stopping the test at 10 grams load if yield stress is evident, this technique is widely ignored and loads up to 150 grams are imposed.

Thus, it seemed timely to develop and evaluate rheological information from a new, higher shear stress instrument. Since high shear stress analysis was not expected to be sensitive to the structural effects of gelation, the test method was developed to accumulate the desired information over a period of only three hours scanning time from −5° to −45° C.—markedly faster than either the SBT or, particularly, the MRV/TP-1.

The Third Zone in the engine is addressed. The present LTEP cold-room pumpability studies used the pressure developed at certain locations in the engine as criteria of performance. Thus, the so-called Third Zone of engine response, shown schematically in FIG. 1 and noted in the SAE Paper No. 770372, was involved. In general, the Third Zone is that zone consisting of the flow from the pump to the lubrication site through the oil supply galleys of the engine. Shear stresses in this region, downstream from the oil pump, are considerably higher than the shear stresses required to induce flow of oil to the pump from the sump under the combined influence of gravity and atmospheric pressure.

The Third Zone shear stress is approximated. To develop correlation with flow in the Third Zone, it was considered necessary to increase the shear stress on the oil to higher levels than could be developed in either the MRV (525 Pa) or low shear stress version of the SBT (70 Pa).

In choosing a suitable instrumental approach, it was evident that there were a variety of temperatures at which the engine pumpability tests were run. Thus, it would be helpful to have a viscometric method that would generate the whole viscosity-temperature profile in one test. Consequently, this led to the development of a higher stress version of the SBT. This new technique, again, is called the moderately high shear stress Scanning Brookfield Technique (once again, MHS/SBT). It operates at shear stresses up to approximately 1000 Pa.

The higher shear stress viscometry at low temperatures is further described below.

Newtonian behavior of oils may occur in theory and/or practice. With a Newtonian oil, by definition, variation in shear stress will have no effect on its viscosity at any given temperature. Moreover, the viscosity-temperature curve will have a smooth exponential change.

Shear-thinning oils may be encountered. In the case of a non-Newtonian oil devoid of significant gelating characteristics but with a VI-Improver, the apparent viscosity measured will depend on the shear sensitivity of the blend. In turn, the shear sensitivity will depend on the following factors:

1. the molecular weight of the VI-Improver;
2. the concentration of the VI-Improver;
3. the viscosity of the base oil at the temperature at which the viscosity is determined; and
4. the level of shear stress imposed by the viscometer.

Figure 2:
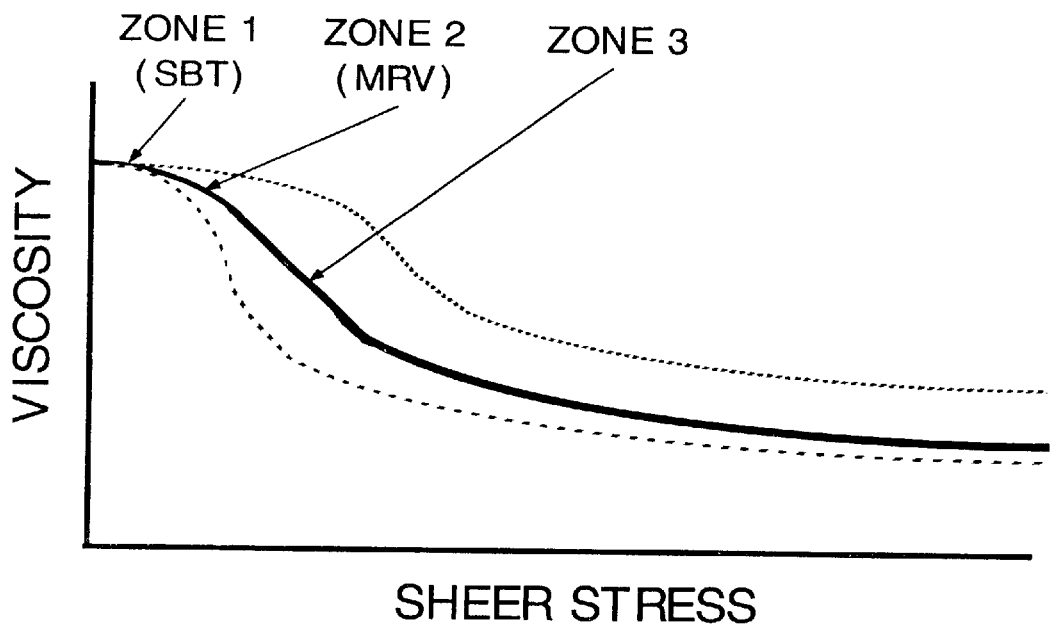
FIG. 2 is a graph showing shear-thinning dependence of viscosity on shear stress for a VI-improved engine oil at low temperature and higher viscosity.

A sketch of the well-known nature of this so-called "shear-thinning" relationship between apparent viscosity and shear stress is shown in FIG. 2 with an indication of relative shear stresses of the three zones of pumpability.

It will be noted from FIG. 2 that for this type of oil (shear-thinning without the presence of gelation), there may or may not be a large difference in apparent viscosity between the zones depending on the shear stress at which the first shoulder occurs for the given oil (cf., dashed curves in FIG. 2).

If the shoulder occurs at stresses higher than the maximum shear stress of the MRV (as shown by the heavy curve in FIG. 2), correlation between the SBT and the MRV would be expected to be high for mildly shear-thinning oils (in the absence of any gelation) but poorer for oils having higher shear-thinning characteristics. In addition, the higher the viscosity of the oil the higher the shear-thinning response—that is, the lower the apparent viscosity.

Figure 3:
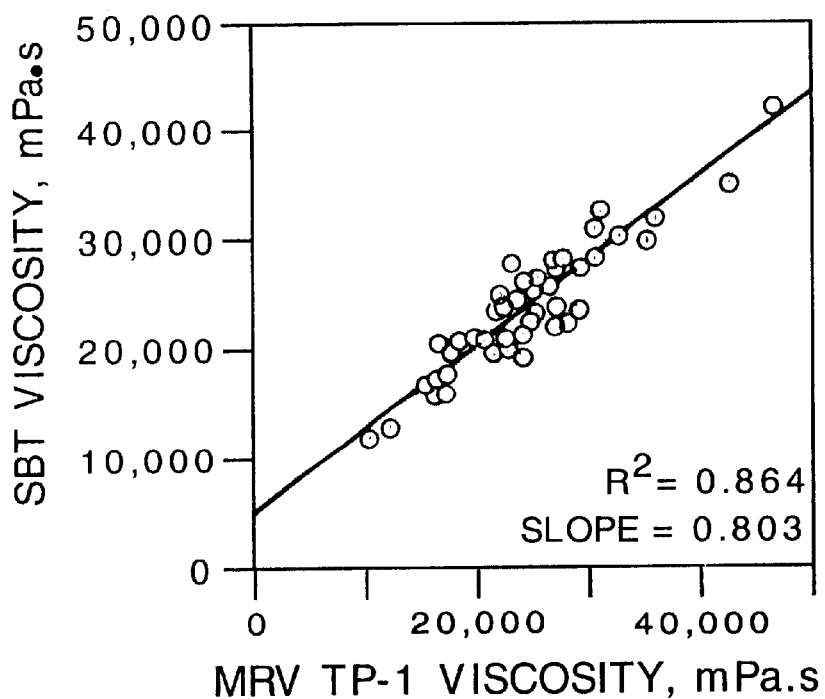
FIG. 3 is a plot showing correlation of MRV and SBT viscometers for non-gelating oils of shear-thinning character, with data from Institute of Materials (IOM), Inc. database of 1997 (used with permission).

This is actually the case as shown in FIG. 3. None of the oils used in building the correlation in FIG. 3 showed evidence of forming gelation at or before the temperature of comparison.

Figure 4:
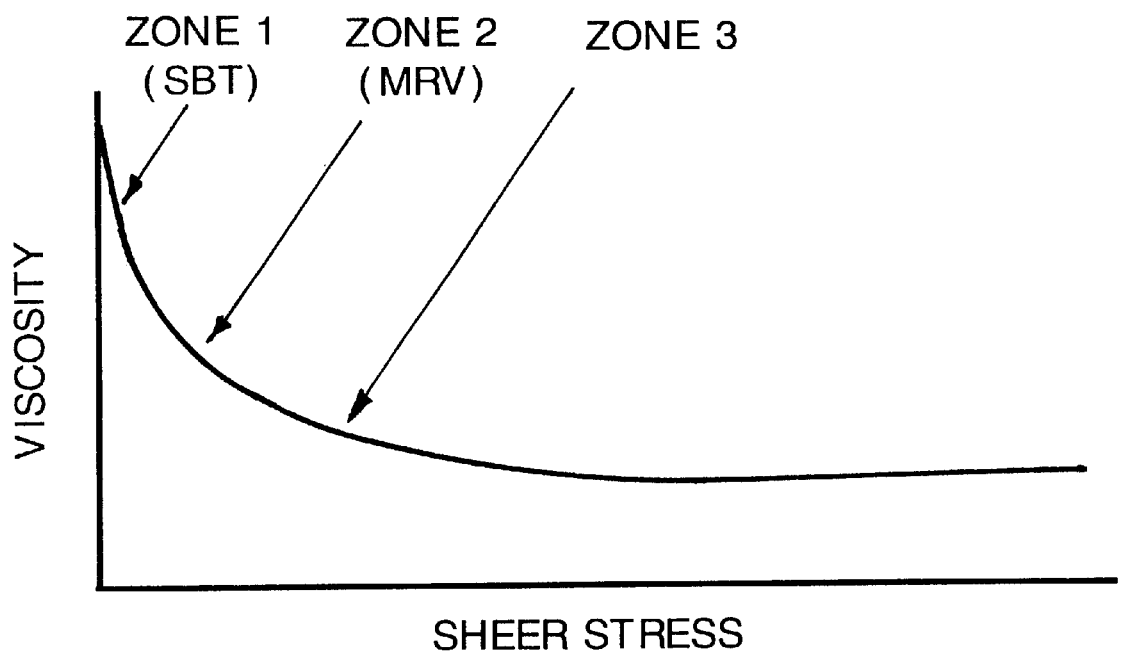
FIG. 4 is a plot showing dependence of viscosity on shear stress for a gelated engine oil at low temperature and higher viscosity.

With respect to gelating oils, if a non-Newtonian oil has only gelating characteristics, increasing levels of shear stress will cause an exponential decay in the level of viscosity. This is illustrated in FIG. 4. It can be seen that for gelated oils the viscosity difference between Zone No. 1 and Zone No. 2 can now be large while the difference between Zone No. 2 and Zone No. 3 can be relatively small. Thus, the SBT would be expected to be poor in reproducing conditions of Zone No. 3 while the MRV may be a closer approximation, depending on the strength of the gel structure.

Combinative rheology is often encountered in practice. Most commercial oils are multi-grade and any of these that show gelation will also be shear thinning. Consequently, they would be expected to show mixtures of behavior combining features of both forms or rheological behavior.

A Higher Shear Stress Test Method

The equipment and methodology are listed below.
I. Viscometer Head and Rotor/Stator Cell A specially selected, higher-torque, Brookfield Viscometer head was used. This viscometer head produces a shear stress of 995 Pa at a shear rate of one reciprocal second.

The rotor/cell is as described in ASTM Method D 5133. Operating speed of the rotor was 1.5 rpm. Compare, FIG. 35.
II. Low-Temperature Liquid Bath To reduce the test time, a bath capable of reliably and precisely cooling the samples rapidly was required. At these high cooling rates, the bath also had to provide reasonably homogeneous temperature throughout the bath fluid. Two known baths that would meet these rigorous conditions of rapid cooling and relatively homogeneous temperature control were the Research Model PlusTwo and Production Model PlusEight baths manufactured by Tannas Co. Both were available for use, but the Research Model PlusTwo was chosen for simplicity since only one viscometer head was needed for these tests.
III. Data Collection As noted previously, the basic Scanning Brookfield Technique of ASTM D 5133 was used with the exception of a special viscometer head having much higher torque capacity, the rapid cooling bath, and a proprietary computer program modeled for Savant, Inc. by the Tannas Co. on the platform of the program for ASTM D 5133. This program collects analog torque and temperature data, digitizes it and then calculates and records viscosity, temperature, the double logarithm of the viscosity, the logarithm of the temperature in degrees Kelvin, and the Gelation Index and Gelation Index Temperature.

IV. Oils Used in Correlation Study

Most of the oils used in the LTEP program were made available and most were used in this study. These included LTEP-1, -2, -3, -5, -6, -7, and the second series, LTEP-21, -22, -23, -24, -26, -27 & -28.

V. MHS/SBT Methodology

The bath is programmed to cool at 15° C. per hour and the motor speed set at 1.5 rpm for the MHS/SBT analyses. Calibration, preheating of the sample and operation of the equipment uses the same techniques as detailed in ASTM Test Method D 5133. Essentially, then, the only differences between the higher stress method presented in this embodiment and that of D 5133 is that a much higher shear stress head is used, the sample is cooled at 15° C./hour from −5° to −50° C. and the rotor speed is 1.5 rpm. After three hours, the automated program ends and records the data collected on a magnetic disk.

RESULTS

I. Viscometric Results

A. Study of the Rheology of LTEP-28 Reference Oil

The first task in the present study was to compare the rheological results at different shear stresses form the analyses of a non-Newtonian oil. For this, LTEP-28 was chosen, an oil which was both shear-thinning and showed moderately high gelation. It was also the oil most similar to the field-failing oils mentioned earlier. Compare, Rhodes et al., personal correspondence marked Apr. 9, 1997, which discusses aspects of pumpability experiments mentioned in Resio et al., "A New Instrumental Approach to the Determination of Yield Stress of Engine Oils and Other Lubricants, 1997 SAE International Spring Fuels and Lubricants Meeting, Dearborn, May 5–8, 1997.

In FIG. 5, results from the MHS/SBT technique are compared to the lower stress SBT (ASTM D 5133). Finally, as a very high shear stress value (~100,000 Pa), the data were compared to results from the CCS using a step-scan approach. In this test, the ASTM D 5293-92 method is used to obtain a first viscosity value at the appropriate temperature. Following this, while the viscometer is still operating, the stator is heated to zero degrees C, and temperature equilibrium is re-established, following which, equilibrium readings are taken by lowering the temperature in 5-degree-C-steps until the viscosity value reaches 5,000 to 7,000 cP, at which point the step-scan CCS test is ended.

Gelation response—In FIG. 5, the SBT results show moderately strong response to the formation of gelation with an evident and gelation-related "ogee" shape 20 at a temperature beginning at about −16° C. Compare, the ASTM Res. Rpt. D02-1261, Annex 4; the SAE Paper No. 852115. As a consequence, it is evident that the three viscometric approaches differ considerably. For example, at −20° C., the apparent viscosities of the oil measured by the SBT, the MHS/SBT, and the CCS at their respective shear stresses are 47700 cP at 70 Pa, 4330 cP at 1000 of gelation at about −17° C. since at temperatures before gelation begins, for example, at −10° C., the viscometers gave quite similar apparent viscosities (1034, 1099, and 706 cP, respectively at the widely different shear stresses just mentioned). Data collected indicate that the MRV/TP-1 also shows this oil to be markedly gelated.

SBT results on LTEP-28—As would be expected from the viscosity-temperature scan in FIG. 5, the normal SBT (ASTM D 5133) indicated a substantial Gelation Index of 31.8 at −17° C. as shown in FIG. 6. This was well into the field-failing region found for engine oils causing the 1980–81 epidemic of pumpability failures.

MHS/SBT results on LTEP-28—Interestingly, the MHS/SBT test showed some gelation at essentially the same temperature of −17° C., as is evident in FIG. 7.

B. Study of the Rheology of LTEP-1 Reference Oil

Oils which show no gelation tendencies are the most common commercial engine oils on the basis of data in the IOM, Inc. Engine Oil Database. In contrast to LTEP-28, it was of interest and value to evaluate LTEP-1, one of only two non-gelated oils used in the ASTM LTEP study.

Viscosity-temperature comparison—FIG. 8 shows the viscosity-temperature plot of LTEP-1 Reference Oil using the same three measures of low-temperature rheology—MHS/SBT, SBT, and CCS. The oils how a smoothly exponential increase in viscosity with temperature and there is little difference in viscosity between the low shear stress SBT and the MHS/SBT operating at more than ten times the shear stress. However, the curve resulting form the very high shear stress results produced by the CCS (shear stresses more than 100 times greater than MHS/SBT) reflects the influence of the shear-thinning response of the oil. See, FIG. 2 and accompanying explanation.

Gelation analysis—Since no evident gelation is visible in the curves of FIG. 8 for LTEP-1, it is not surprising to find that the Gelation Index curve plotted in FIG. 9 is essentially linear and horizontal and, thus, shows no evidence of significant gelation. Consequently, there is no actual Gelation Index peak evident, and the average Gelation Index for the line is 3.0.

The comparatively low value of the average Gelation Index, 3.0, is indicative of a relatively low rate of change of viscosity with temperature.

C. Repeatablility Study

Choice of LTEP-26 for precision study—With the foregoing information in hand regarding the effectiveness of higher shear stress analysis, it was important to establish the precision of the new MHS/SBT approach to measuring apparent viscosities in the Third Zone. Accordingly, another of the gelation-prone reference oils, LTEP-26, was chosen. It was chosen on the basis of having moderate gelation characteristics using the MHS/SBT method. Moderate curves are both clear, have evident inflection points and are sufficiently torque-sensitive which would provide the greatest challenge to obtaining replication as well as comparison and contrast to LTEP-28.

Evaluation of LTEP-26 at three shear stresses—FIG. 10 shows the three viscosity-temperature curves from the three different shear stress instrumental approaches. In this work, several of the CCS values were obtained by extrapolation to show comparison to the MHS/SBT and SBT curves.

In contrast to LTEP-1 but similar to LTEP-28, in the results shown in FIG. 8, LTEP-26 shows the gelation-related "ogee" curves 20 for both the MHS/SBT at 15° C./hr and the SBT at 1° C./hr.

In further regard to the analysis of LTEP-26, FIG. 11 reinforces the previous observation concerning the gelation-related "ogee" curves 20 by showing the corresponding Gelation Index curve using the ASTM D 5133 Scanning Brookfield Technique. As in the case of LTEP-28, LTEP-26 shows evident gelation with a Gelation Index of 25.9 at −11° C. Again, data collected indicate that the MRV/TP-1 also shows this oil to be markedly gelated.

Repeatability of viscosity-temperature curves—Three analyses were made of LTEP-26 using the MHS/SBT method. One early test run followed careful calibration of the special Brookfield viscometer head employed in the practice of the invention. Seven months later the need to replicate this first run was met by a second operator who, after calibrating the special head, ran two back-to-back analyses. Results of the three tests are shown in FIG. 12.

Repeatability of the viscosity-temperature test results carried out over the substantial time period between the first and second analyses look reasonably good. However, a more exacting test of repeatability is generated by plotting the Gelation Index curves derived from these viscosity-temperature plots. Compare, the SAE Paper No. 910746. These Gelation Index plots are shown in FIG. 13. The Gelation Indexes of the three tests on LTEP-26 shown in FIG. 13 range from 9.8 to 10.3 at Gelation Index Temperatures of −11.6 to −11.9° C. This is considered to be good replication and indicates that the MHS/SBT approach has acceptable precision. Again, as in the case of LTEP-28, the Gelation Index Temperature of the MHS/SBT agrees very well with that shown by the SBT in FIG. 11.

D. Rheology of Remaining LTEP Reference Oils

From the information presented, it is evident that the characteristics of the LTEP Reference Oils can be reduced to whether or not they have gelation tendencies and to what degree. TABLE 2 shows this information for all the LTEP Reference Oils evaluated herein using the MHS/SBT method:

TABLE 2

Rheological Properties of LTEP Reference Oils

| Oil | Normal SBT Analysis | | New MHS/SBT Analysis | |
|---|---|---|---|---|
| | Gelation Index | Temperature, ° C. | Gelation Index | Temperature, ° C. |
| LTEP-1 | 4.1 | Nm* | <4 | Nm |
| LTEP-2 | 12.2 | −21 | 7.7 | −21.4 |
| LTEP-3 | 5.6 | Nm | <6 | Nm |
| LTEP-5 | 12.4 | −10 | <5 | Nm |
| LTEP-6 | 23.4 | −11 | <5 | Nm |
| LTEP-7 | 12 | −7 | <6 | Nm |
| LTEP-21 | 56.9 | −13 | 21.6 | −12.9 |
| LTEP-22 | 13.8 | −21 | 7.1 | −19.6 |
| LTEP-23 | 17.8 | −22 | <6 | Nm |
| LTEP-24 | 23.4 | −20 | <6 | Nm |
| LTEP-26 | 25.9 | −11 | 10.3 | −11.7 |
| LTEP-27 | 56.6 | −14 | <5 | Nm |
| LTEP-28 | 31.8 | −17 | 9.7 | −17.7 |

*Nm: not meaningful.

From TABLE 2, four of the first six oils (LTEP-2, -5, -6 & -7) show gelation in the low shear stress SBT study using ASTM D 5133. However, only one of the six (LTEP-2) shows significant gelation in the considerably higher shear stress MHS/SBT study.

In the second set of LTEP oils (LTEP-21, -22, -23, -24, -26, -27 & -28), all of these showed gelation with SBT Gelation Indexes ranging from 13.8 to 56.9. Of these, four showed Gelation Indexes with the MHS/SBT as shown in FIG. 14. In this figure, LTEP-21 stands out with a MHS/SBT Gelation Index value of 21.6 at −12.9° C. This propensity to form gelation could have made the oil the study's prime candidate to show air-binding. Reportedly, this oil did show failure in ancillary pumpability tests but was not tested in the ASTM pumpability study because it was an SAE 15W40 oil that had originally been submitted for heavy duty engine pumpability testing, work that has yet to be supported. In contrast to LTEP-21 is LTEP-27, which had an equally high SBT Gelation Index which disappeared with MHS/SBT analysis. One reasonable interpretation is that LTEP-21 has the propensity to quickly form a gelation structure while LTEP-27 requires more temperature-stable conditions.

Another observation is that when an oil shows gelation in both the SBT and MHS/SBT tests, the Gelation Index Temperature is essentially the same, as shown in FIG. 15.

II. Summary of Rheological Data

As expected, the higher shear stress Scanning Brookfield Technique, MHS/SBT, was shown in these studies to always give either equivalent or lower viscosities than the low shear stress SBT. In general, the higher the gelation of the LTEP oil used, the greater the divergence between the higher shear stress and the lower shear stress technique.

Moreover, in the case of significant gelation, (i.e., Gelation Indexes above 7) in the low shear stress SBT, the Gelation Index Temperatures were essentially the same as at higher shear stress (FIG. 15). This showed that when the much higher cooling rate of the MHS/SBT generated a gelation response, the response occurred at essentially the same temperature. It would seem that the higher cooling rate did not distort the temperatures imposed on the oil being analyzed. That is, the higher cooling rate still seemed to maintain appropriate temperatures in the oil as indicated by the Gelation Index Temperature.

The fact that several of the oils showing gelation at lower shear stress and lower cooling rates did not show gelation response at higher cooling rates and stresses is a reconfirmation of the earlier developmental work on the SBT where lower cooling rates, particularly, were critical in revealing the potential to cause air-binding.

In contrast to what can be obtained hereby, standard gelation-sensitive viscometers such as the SBT and the MRV/TP-1 which were developed to assist the formulation and marketing of non-gelating oils should not be expected to correlate with engine pumpability tests which show little or not gelation response. Low-temperature engine pumpability data requires viscometric devices emulating the engine for appropriately acceptable correlation and the following correlation study shows this approach.

III. Correlation Study

A. Basis of Comparison

Generally, comparison of two groups of data that are presumably measuring the same property will give correlation dependent on how precisely each set of measurements are gathered. Imprecision in one will degrade the correlation of both. Precision in both will show more clearly the correlation that actually exists between them.

One of the measures of correlation between two sets of measurements is a term called the Coefficient of Determination, $R^2$, which is, roughly, a measure of interdependency of two variables—how much variation in one affects variation in the other. Thus $R^2$ can be used to measure changes in interdependency as the conditions of measurements change. More importantly, $R^2$ can be used as a guide to improving understanding of the relationship between variables. For example, past work with instruments showing high gelation sensitivity also showed $R^2$ values from 0.76 for the MRV/TP-1 to 0.96 for the SBT in correlating with the first ASTM engine pumpability tests in the 1970s. Compare, the 10/94 Henderson handout; the SAE Paper No. 922287.

B. Viscometric Data

Upon completing an MHS/SBT test, viscosities were selected at the various temperatures at which the engine pumpability data had been taken. These were the viscosity values used to build up the correlation data for all of the engine tests on each particular reference oil.

Using a temperature-scanning technique saved much time in not having to obtain temperature by temperature data but rather obtaining a range of viscometric data in one test for correlation to the broad range of temperatures at which pumpability data were collected.

C. Engine Pumpability Information

Pumpability data from only two test facilities using two different engines were considered sufficient to develop correlation with the viscometric information disclosed hereby. As the criteria of pumpability, employed were the time required for galley pressure to reach 100 KPa at three locations in the engine:

1. the nearest galley supplying oil to the cam shaft area (called the "near-cam" pressure),
2. the pressure after the filter upstream form the near cam galley (called the "filter-out" pressure), and
3. the pressure in the line between the pump and the filter (called "pump-out" pressure).

D. Laboratory A Engine Pumpability Correlation

Correlation using near-cam galley pressure—By the time the oil has reached the near-cam galley location, it would seem reasonable that it would have gone through considerable homogenization if structures existed. Consequently, this was the first area in which correlation was sought. It is the area in which the apparent viscosity of the oil may be most affected by the shear stresses of flow.

FIG. 16 is a plot of data from Engine 1 operated by Laboratory A using several of the LTEP Pumpability Reference Oils. As mentioned earlier herein, the time to reach 100 KPa pressure in the near galley was plotted against viscosity using the MHS/SBT method. The correlation appears good with a Coefficient of Determination, $R^2$, of 0.80, an intercept of 5,870 cP, and a slope of 1037 cP/s —the latter value being a measure of sensitivity when comparing correlation between viscosity and pump-up time.

Correlation at the Filter Outlet—Stepping back toward the pump in the Third Zone, correlation was developed between flow time to reach 100 KPa at the filter outlet and the same set of viscometric data using the MHS/SBT method. Since this engine area provided oil for the galleys including the near-cam galley, it might be expected that correlation might approach that of the near-cam galley. Results are shown in FIG. 17.

Again, the data show good correlation—essentially equivalent to the near-cam pressure data. The Coefficient of Determination, $R^2$, is 0.78, the intercept is 6350 cP, and the slope is 1758 cP/s.

Correlation at the Pump Outlet—Moving still further upstream toward the oil pump, correlation was determined using the time required to reach 100 KPa pressure in the earliest portion of the Third Zone—between the pump outlet and the filter. Results are shown in FIG. 18.

For the first time it is evident that correlation is relatively poor with $R^2=0.20$ coupled with a high intercept (zero being the ideal intercept) and a slope of 6279 cP/s. One of the most likely causes for the poor correlation is the relatively brief time required to reach 100 KPa.

In any case, when seeking correlation with viscosity, the area of the Third Zone between the pump and the filter does not seem to be a suitable site for testing engine pumpability pressures, at least in regard to Engine 1.

E. Laboratory B, Engine 2, Pumpability Correlation

It was important to determine if the correlation obtained with the pumpability tests shown in FIG. 15 would be repeated with data from another engine and test sequence. Thus, data from Laboratory B using a different engine design were evaluated using the MHS/SBT method.

The near-cam galley pressure used to evaluate Engine 1 in Laboratory A was used to evaluate correlation with Engine 2 of Laboratory B. Fewer test results were generated on this engine. Results are shown in FIG. 19.

Considering the smaller set of pumpability data compared to those from Engine 1 of Laboratory A, correlation is acceptable at $R^2=0.70$.

IV. Low Shear Stress SBT Method Correlation Studies

It was of some interest also to determine whatever correlation could be found between the pumpability data and the SBT data. Compare, FIG. 20, which correlates minimum SBT temperature to engine-pumping temperature. Note, the well known MacCoull, Walther, Wright equation. See, e.g., Wright, "An Improved Viscosity-Temperature Chart for Hydrocarbons, Journal of Materials, JMLSA, Vol. 4, No. 1, 1969, pp. 19–27, citing MacCoull, Lubrication, The Texas Co., New York, 1921, p. 85; Walther, Erdöl, und Teer, Vol. 4, 1928, p. 510. This equation uses the double logarithm (LogLog 'x') of the viscosity plotted against the logarithm of the absolute temperature in degrees Kelvin (Log ° K.) to develop a linear plot of the data. If the SBT analysis can measure the complete gelation development process before exceeding the torque limit of the viscometer head, the linear portion following the gelation discontinuity can be extrapolated as shown as in FIG. 21.

Considering the method of obtaining the viscosity data from the SBT, the correlation is surprisingly good but still marginal with an $R^2$ value of less than 0.60. Certainly, use of the low shear stress SBT method is not recommended for correlation with pumpability results from engines in which gelation is either absent or ignored.

V. Summary of Correlation Study

A. MHS/SBT Correlation with Engine Pumping Data

The correlation study has shown that the relatively fast MHS/SBT method produces viscometric data which correlate well with the engine pumpability results gathered in the LTEP study on two engines, Engine 1 of Laboratory A, and Engine 2 of Laboratory B. In the more extensive evaluation of correlation using Engine 1, it has also been shown that correlation deteriorates with pressure-rise-time data taken very near the pump outlet.

Engine 2 supported the observations in the first correlation study.

B. SBT Correlation with Engine Pumping Data

Regarding the correlation of the gelation-sensitive SBT method with the ASTM LTEP pumpability data, the results have shown that the low shear stress, slow-cooling SBT data obtained by ASTM D 5133 are not appropriate for engine pumpability studies in which classic gelation is either not formed or is ignored by the engine under the cold-room test conditions applied.

From limited data, this conclusion seems likely to be the case for the MRV/TP-1 protocol as well.

Discussion

I. Methodology

MHS/SBT Method Development—The method that was developed was conceived as a much higher shear stress, higher analytical speed version of the SBT. Among other uses, such an approach would be expected to correlate with results from the LTEP engines which, as noted earlier, showed no evident gelation influence.

The MHS/SBT thus provided viscometry more closely simulating the shear stresses in the Third Zone of the engine. The method imposed shear stresses up to 1000 Pa at the temperatures required in the pumpability tests and furthermore provided continuous viscosity values across the temperature range of interest in three hours analysis time.

A more significant application, however, was that the same higher shear stress technique with its rapid acquisition of information would augment the gelation-sensitive SBT method (ASTM D 5133) in production control. That is, once a formulation was developed using the SBT, the MHS/SBT would provide rapid confirmation of the low-temperature acceptability of production oils.

Residual gelation at higher shear stress—While most of the LTEP oils showed some degree of gelation when analyzed by the SBT method D 5133, it was interesting that some of the oils continued to show this response, albeit at reduced levels with the MHS/SBT method at essentially the same Gelation Index Temperatures. In fact, one of the oils, LTEP-21, exhibited a fairly high Gelation Index of 21.6 under the higher shear stress conditions.

Shortened test time—The MHS/SBT method was shown to be capable of analyzing an engine oil for pumpability-related performance in three hours from $-5°$ to $-50°$ C. This required a high-performance low temperature bath capable of cooling at least at approximately $20°$ C./h over the temperature range.

II. Viscometry and Correlation with Pumpability Tests

Third Zone correlation—The MHS/SBT method was believed appropriate to provide conditions simulating the flow conditions in the Third Zone. Availability of the pumpability data from the LTEP permitted testing the degree of correlation with oils and engines relatively free from gelation influence.

MHS/SBT correlation—The resulting correlation study showed that the MHS/SBT method did correlate with the engine pumpability data for two engines at levels of $R^2=0.80$ for Engine 1 (with 36 data pairs) and $R^2=0.70$ for Engine 2 (with 16 data pairs). This was sufficient to establish the relationship between the instrument and the engine data.

Both cooling rate and shear stress were changed in developing the MHS/SBT (or SBT-XR) methodology and device.

Note for comparison purposes, Wheeler et al. (Eds.), "Low-Temperature Pumpability Characteristics of Engine Oils in Full-Scale Engines," ASTM Data Series DS 57, Data Analysis Panel RDD 7C, ASTM, September, 1975; Shaub et al., "Predicting Low Temperature Engine Oil Pumpability with the Mini-Rotary Viscometer," SAE Paper No. 790732, SAE Passenger Car Meeting, Dearborn, Jun. 11–15, 1979; Shaub et al., "Mini-Rotary Viscometer and Engine Oil Pumpability," STLE 35th Annual Meeting, Anaheim, May 5–8, 1980; ASTM D 3829-93.

III. Very Recent Developments

A. Oxidized Oils

The effort to extend engine drain intervals in engines running considerably hotter than ever, has been recently shown to be limited by the effects of oxidation on pumpability. Exhaust gas recirculation is also a factor.

In North America where leasing of vehicles is very widespread, the combination of hotter engines plus frequent lack of ownership incentive related to oil drain intervals has led to engines being run thousands of miles beyond a reasonable drain interval. The consequence is that crankcase oils are thoroughly oxidized with viscous characteristics at $+20°$ C. and below, showing the potential for serious pumpability difficulties coupled with filter plugging.

FIG. 28A shows the use of an extended viscosity and temperature range Scanning Brookfield Technique (SBT-XR) study of two very extended drain samples form the same engine taken at 33,000 and 36,000 km. The 33,000-km sample was the earliest available and the poor condition of the oil at 33,000 km and the changes in the character of the oil over a 3,000-km interval is very evident. For both oils, arrows 23 show noticeable changes in the slope of the curve. Both oils have at least two arrows 23 over the temperature range up to 100,000 cP plotted in FIG. 28A.

The Gelation Index curves of the two oil samples of FIG. 28A are shown in FIG. 28B. It will be noted that the 36,000-km sample shows three Gelation Index peaks, of which the highest temperature peak is most pronounced. This oil physically showed considerable "lumpiness" when poured at about $20°$ C., and it was known that the oil had plugged the oil filter which resulted in considerable bearing damage.

Repeatability of these Gelation Index curves is shown in FIG. 29. The curves replicate reasonably well considering that they are derivatives of viscosity-temperature data showing considerable gelation at different temperatures. Both the height and the temperature correspond well even to the presence of a double peak in Gelation Index at about $-8°$ to $-12°$ C. The peaks seem associated with the development of oil "lumpiness" and filter plugging.

B. Highly Sooted Oils

As a consequence of recent U.S. government mandates on lowering oxides of nitrogen and including the 13-mode European cycle in the test sequence, soot will become a much greater problem. Since nine percent soot is not at all uncommon in diesel engine tests, concerns have been raised that such levels of soot could have serious adverse effects on the diesel engine oil pumpability among several other important effects. McGeehan et al., in the SAE Paper No. 1999-01-1525, showed, among other observations and data, that concern about pumpability of highly sooted oils was warranted.

Addressing the issue of pumpability with several commercial 15W40 blends, they used single values from MRV/TP-1 at the required temperature of $-25°$ C. However, to understand what was happening over the range of temperatures and viscosities from $+20°$ C. down to temperatures producing viscosities in the range of a million cP, they applied the Broad Range Scanning Brookfield Technique (SBT-BR) (a.k.a. SBT-XR) developed by the present inventor to measure the rheology of oils over an extended range of viscosity and temperature.

IV. Response to Present and Future Pumpability Bench Test Needs

A. Extended Range Scanning Brookfield Technique—Experimental Work

The above-detailed extended viscosity range version of the Scanning Brookfield Technique showed that this approach was not only feasible but that even further extension could be considered. Consequently, a special method called the Scanning Brookfield Technique Extended Range (SBT-XR) method was developed with particular Brookfield heads and analysis programs. The method has been recently applied to several engine oils included in the IOM, Inc. Engine Oil Database. These oils were run in the SBT-XR mode in comparison to the standard SBT results used in present specifications and shown in the IOM Engine Oil Database. The range of the SBT-XR is about 800,000 cP at $1.7\ s^{-1}$ shear rate and the temperature range of the low temperature bath used was from $+30°$ to $-75°$ C.

B. Comparison of Fresh Passenger Car Engine Oils Using the SBT and SBT-XR Protocols Well-Behaved Oils—The following data were gathered on a set of well-behaved (non-gelated) oils using the SBT-XR, the SBT, and the MRV/TP-1 to determine how well the instruments agree when gelation is not present. These fresh oil tests were run primarily to determine the degree of correlation between the standard SBT and the SBT-XR.

FIG. 30A shows the extended curve for Engine Oil K, a mineral-oil-based SAE 10W40. The MRV/TP-1 value obtained at 30C° is also shown as an open circle. The SBT-XR curve has the smoothly exponential shape associated with a well-behaved oil showing no gelation tendency. It will be noted that the value for the MRV/TP-1 falls close to the SBT-XR curve as would be expected for simple, non-gelating oils.

A dashed horizontal line in FIG. 30A is the upper limit for the expanded section shown in FIG. 30B. Even with this magnified view, the data from the SBT-XR shows a smooth line. Moreover, the results of the standard range SBT data (obtained from the database of IOM, Inc.) shown in this latter figure, also falls in good agreement with the SBT-XR. Again, the MRV/TP-1 value is plotted and falls in close agreement with both.

FIG. 30C shows the associated Gelation Index curves with maximum values from 4 to 5. The general forms of the curves are similar.

In general, the data of FIGS. 30A & 30B indicate that the curve generated by the extended-range SBT-XR fits encouragingly well with the normal range SBT. Moreover, as would be expected for a well-behaved mineral oil, the SBT-XR, SBT, and MRV/TP-1 data agree well.

Engine Oil G—Synthetic-Oil Based SAE 5W50—Comparison of the three instrumental modes of low-temperature viscometric analysis using a synthetic oil is shown in FIGS. 31A, 31B & 31C.

Again, the plotted data in FIGS. 31A & 31B show that the SBT-XR and the MRV/TP-1 values agree fairly well. Similarly, the more recent data obtained from the SBT-XR agree reasonably with the SBT data published earlier by IOM, Inc.

The Gelation Index values for both the SBT-XR and the SBT are in good agreement and essentially horizontal over most of their range, thus showing no gelation tendency. The degree of agreement was considered to be even more promising considering the viscosity range over which this oil was measured. It would appear that the concept and application of the Gelation Index extends over a broad viscosity range.

Oils with Gelating Tendencies—At this point in the exploration of the application of the SBT-XR, it was appropriate to apply the technique to oils which had the capacity of forming gelation. Two SAE 15W40 engine oils were chosen for this study, one of which was known from the IOM data base to have a significant Gelation Index of 37 and the other of which had a relatively low Gelation Index of 14.

Engine Oil A—SAE 15W40 (Higher Gelation Tendencies)—The SBT-XR data on this oil produced the curve shown in FIG. 32A. An evident "ogee" curve 20 was generated as would be expected with an oil having significant gelation. In agreement with this information, the MRV/TP-1 showed a yield stress of 175 and 210 Pascals in two tests. The viscosity is considerably lower than the value shown by the SBT-XR curve. However, the viscosities of the two tests on the MRV/TP-1 agreed closely, as is evident.

When the lower 100,000 cP section of FIG. 32A is expanded as shown in FIG. 32B and the SBT data added for comparison, it may be seen that the data from the SBT-XR and the SBT agreed closely, to the point where the curves virtually lie on top of one another.

This agreement was further demonstrated by determining the Gelation Index obtained for Oil A from both the SBT-XR and the SBT. These curves are shown in FIG. 32C. Again, it is evident that the agreement of the considerably lower torque SBT and the much higher torque SBT-XR is very close despite the difference in torque range. The Gelation Indexes and Gelation Index Temperatures are 36.5@−16.2° C. and 37.9@−15.6° C. for the SBT-XR and the SBT, respectively. This is well within the precision given in the ASTM D 5133.

Engine Oil D—SAE 15W40—(Lower Gelation Tendencies)—It was of further interest to see what correlation would be found between the two Scanning Brookfield Technique protocols, SBT-XR and SBT, when used with an oil having a lower level of gelation. This comparison was particularly interesting considering the fact that the higher torque range of the SBT-XR method might reduce sensitivity to mild gelation.

It can be seen in FIG. 33A that Oil D shows only a slight "ogee" 20 in its curve. The remainder of the curve takes on the familiar exponential form. Data obtained on the MRV/TP-1 is again displaced to lower values of viscosity.

When only the section of the curve below 100,000 cP is used, the "ogee" portion 20 of the curve is made considerably more evident as shown in FIG. 33B.

Regarding the level of agreement of the two different SBT protocols, FIGS. 33B & 33C show that agreement between the two SBT methods is surprisingly good. The higher level of torque applied in the SBT-XR seems to give equivalent sensitivity to gelation as the original SBT even at low gelation levels.

Comparing the numerical values obtained, the Gelation Indexes and Gelation Index Temperatures are 14.9@−14.1° C. and 15.5@−13.9° C. for the SBT-XR and the SBT methods, respectively. This again is well within the precision of ASTM D 5133. With this information it seems apparent that the SBT-XR is applicable to a range of pumpability concerns.

The value of the MRV/TP-1 shown in FIGS. 33A & 33B is considerably lower than either the SBT-XR or even the original SBT. No yield stress was found by the TP-1 with this oil, but at the low level of Gelation Index this was not surprising since yield stress is not often found below a Gelation Index of 25. This lack of correlation with mildly gelating engine oils supports the previous observation that the SBT, generally, is more sensitive to gelation. However, a few oils have been found in which the converse is true, i.e., the TP-1 is a more sensitive test.

C. Broad Application of the SBT-XR

It would appear from this new SBT work that although the experimental SBT-XR has a greater range of viscosity, little is lost regarding sensitivity to gelation. The high level of agreement between the SBT-XR and the normal range SBT is surprisingly good since the use of the incremental derivative is a strong test of sensitivity and precision of the instrument and method.

With this data showing the range and precision of the SBT-XR, application to used oil seems important, particularly with the rising level of concern about low-temperature pumpability of both oxidized passenger car engine oils and highly soot-laden heavy-duty engine oils.

Such subjects important to future questions of controlling engine oil pumpability are considered in the next section.

V. Modem Lubrication Pumpability Problems and Challenges

A. Sooted Oils and Pumpability Problems and Measurements

Background-Relatively recent government mandates for 1999 regarding heavy duty diesel emissions of $NO_x$, have forced the industry to significantly retard engine timing. This has resulted in very high levels of soot in the engine oil as well as other consequences of such soot levels including valve train wear, shortened filter life, and (important from the considerations hereof) loss of engine oil pumpability. The recent, well-developed and penetrating paper by McGeehan and associates documented these factors very clearly, with a clear warning about ignoring the significance of controlling soot.

Although comprising a relatively small part of the extensive work reported by McGeehan et al., in their SAE Paper No. 1999-01-1525, the pumpability aspects and data related to these were considered by them as important to predicting proper engine function and protection. This was particularly the case considering the consequences of poor pumpability at moderate ambient temperatures.

Experimental Pumpability Findings Using the SBT-XR Protocol—The inventor's laboratory was requested to evaluate the rheological nature of these oils and this required use of the SBT-XR method. In particular, it required the method to be applied over a temperature range from 0° C. to −20° C. or more with oils so sooted that viscosities could reach hundreds of thousands.

The data shown in FIGS. 34A, 34B & 34C are taken from the paper by McGeehan et al., and are striking in their rheological differences and the effect of dispersants on these properties. For example, Oils #1 and J are similar in viscosity at 0° C. but very different thereafter with Oil J showing rheological characteristics suggesting either a viscosity-limited or air-binding flow problem for the engine shortly after the temperature reaches −5° C. The Gelation Index indicates a value of 16.

Oil #5, on the other hand, starts at a relatively high viscosity of about 4500 cP at 0° C. but from there becomes better-behaved than Oil J although still not acceptable from the viewpoint of its comparatively high viscosity level.

Oil J, with its evident Gelation Index at about −5° C. also had the same magnitude Gelation Index when fresh at about −9° C. This suggests that while the presence of high soot may not efface the presence of fresh oil gelation, it may move the Gelation Index Temperature to some higher temperature.

Oil #1 is exceptional among the three oils examined with the SBT-XR method in that it retained its exponential character, i.e., was free from evidence of gelation and maintained the lowest viscosity of the three oils tested. It will also be noted that the TP-1 value of this oil fell on the SBT-XR curve, further indicating its freedom from gelation.

B. Conclusions from the Sooted Engine Oil Tests

The results of the latter work on three sooted oils indicates that the use of the SBT-XR in characterizing the rheology of sooted engine oils at moderately low temperatures gives considerable information about the degree of dispersant control. With this bench test it was found that even at a level of 9% soot loading, it is possible for engine oils to retain acceptable control of pumpability at moderate and lower temperature as is evident from the bench data presented here and in the McGeehan et al. paper.

Accordingly, the inventive method can determine a physical property of a liquid test fluid that may include a viscometric and/or rheological property and/or structural physical property that may include gelation and/or crystallization, which employs an extended range rotating viscometer technique and embraces providing a suitable rotary viscometer with a rotor and a stator and having a suitably strong head, which viscometer includes a motor driving a rotor, a stator in which the test fluid is to be contained, with the rotor being driven in the test fluid in the stator, and a temperature-control feature which can control the temperature of the test fluid in the stator during testing; providing the test fluid to the stator, and immersing the rotor in the test fluid in the stator; rotatably contacting the rotor with the sample in the stator by driving the rotor immersed in the test fluid with the motor, typically under high shear stress conditions, while varying the temperature of the temperature-control feature, and hence, the test fluid, as a function of time over a period of about half a day or less for Third Zone correlation and slower cooling for First Zone correlation, with the temperature being lowered throughout the testing from and to a suitably low value; monitoring the stress and/or viscosity of the test fluid during the testing by measuring drag on the rotating rotor; and obtaining data therefrom. Further, such a method can have the viscometer head with a shear stress substantially greater than about seventy Pascals. Further, such a method can be carried out such that a temperature range of +30 degrees C to −40 degrees C or more is scanned through a programmed temperature range, and the shear stress is one thousand Pascals or higher. Thus, for Third Zone correlations, average temperature-lowerings, taken in terms of degrees C per hour, are listed in TABLE 3:

TABLE 3

| Temperature Change, ° C. | Temperature Drop Rates in ° C./Hr. | | | | | |
| --- | --- | --- | --- | --- | --- | --- |
| | Δ | 12 | 8 | 6 | 4 | 3 | 2 |
| +30 to −75 | 105° C. 8¾ | 13⅛ | 17½ | 26¼ | 35 | 52½ |
| +30 to −40 | 70° C. 5⅚ | 8¾ | 11⅔ | 17½ | 23½ | 35 |
| 0 to −60 | 60° C. 5 | 7½ | 10 | 15 | 20 | 30 |
| 0 to −50 | 50° C. 4⅙ | 6¼ | 8⅓ | 12½ | 16⅔ | 25 |
| −5 to −50 | 45° C. 3¾ | 5⅝ | 7½ | 11¼ | 15 | 22½ |
| −5 to −45 | 40° C. 3⅓ | 5 | 6⅔ | 10 | 13⅓ | 20 |
| −5 to −40 | 35° C. 2¹¹⁄₁₂ | 4⅜ | 5⅚ | 8¾ | 11⅔ | 17½ |

As well, the invention can accordingly provide, in another aspect, a head for a rotary viscometer with a rotor and a stator in which a test sample is to be contained, in which the head includes a motor for driving the rotor, and a spring to provide for measurement of drag on the rotor being driven in the test sample in the stator, the improvement can embrace the spring being novel and having a stress adapted for the purposes of the methodology disclosed herein.

Final Conclusion

The present invention is thus provided. Numerous adaptations and modifications can be effected within its spirit, the literal claim scope of which is particularly pointed out as follows:

I claim:

1. A method for determining a physical property of a liquid test fluid that may include a viscometric and/or rheological property and/or a structural physical property that may include gelation and/or crystallization, which employs an extended range rotating viscometer technique comprising: providing a rotary viscometer with a rotor and a stator and having a head with a shear stress of at least about 90 Pa—which viscometer includes a motor driving the rotor, the stator in which the test fluid is to be contained, with the rotor being driven in the test fluid in the stator, and a temperature-control feature which can control the temperature of the test fluid in the stator during testing; providing the test fluid to the stator, and immersing the rotor in the test fluid in the stator; rotatably contacting the rotor with the sample in the stator by driving the rotor immersed in the test fluid with the motor, while varying temperature with the temperature-control feature, and hence, the test fluid, as a function of time, with the temperature being lowered throughout the testing; monitoring the stress and/or viscosity of the test fluid during the testing by measuring drag on the rotating rotor; and obtaining data therefrom.

2. The method of claim 1, wherein the viscometer head has a shear stress of at least about 1000 Pa.

3. The method of claim 2, wherein a temperature range of at least 35° C. is scanned through a programmed temperature range, of which at least a portion lies below 0° C.

4. A method for determining a physical property of a liquid test fluid that may include a viscometric and/or Theological property and/or a structural physical property that may include gelation and/or crystallization, which employs an extended range rotating viscometer technique comprising: providing a rotary viscometer with a rotor and a stator and having a head with a shear stress of at least about 90 Pa—which viscometer includes a motor driving the rotor, the stator in which the test fluid is to be contained, with the rotor being driven in the test fluid in the stator, and a temperature-control feature which can control the temperature of the test fluid in the stator during testing; providing the test fluid to the stator with the test fluid being an engine oil, and immersing the rotor in the test in the stator; rotatably contacting the rotor with the sample in the stator by driving the rotor immersed in the test fluid with the motor, while varying temperature with the temperature-control feature, and hence, the test fluid, as a function of time over a period of about half a day or less for Third Zone correlation, with the temperature being lowered throughout the Third Zone correlation testing through a temperature range of at least 35° C., of which at least a portion lies below 0° C.; monitoring the stress and/or viscosity of the test fluid during the testing by measuring drag on the rotating rotor; and obtaining data therefrom.

5. The method of claim 4, wherein the viscometer head has a shear stress of at least about 1000 Pa.

6. The method of claim 5, wherein the viscometer head has a shear stress of at least about 4000 Pa.

7. The method of claim 4, wherein the temperature range is found within a range from +30° C. to −75° C.

8. The method of claim 5, wherein the temperature range is found within a range of from +30° C. to −75° C.

9. The method of claim 6, wherein the temperature range is found within a range of from +30° C. to −75° C.

10. The method of claim 7, wherein the range is selected from the group consisting of from +30° C. to −40° C; from 0° C. to −60° C.; from 0° C. to −50° C.; from −5° C. to −50° C.; from −5° C. to −45° C.; and from −5° C. to −40° C.; and the period about 2 hours to about 12 hours.

11. The method of claim 8, wherein the range is selected from the group consisting of from +30° C. to −40° C.; from 0° C. to −60° C.; from 0° C. to −50° C.; from −5° C. to −50° C.; from −5° C. to −45° C.; and from −5° C. to −40° C.; and the period is from about 2 hours to about 12 hours.

12. The method of claim 9, wherein the range is selected from the group consisting of from +30° C. to −40° C.; from 0° C. to −60° C.; from 0° C. to −50° C.; from −5° C. to −50° C.; from −5° C. to −45° C.; and from −5° C. to −40° C.; and the period is from about 2 hours to about 12 hours.

13. In a Scanning Brookfield Technique rotary viscometer instrument, which includes a head for the rotary viscometer with a rotor and a stator in which a test sample is to be contained, said head including a motor for driving the rotor, and a spring to provide for measurement of drag on the rotor being driven in the test sample in the stator, and which includes a temperature-scanning feature which can control temperature of the test fluid in the stator during testing such that the temperature of the test fluid can be controllably varied as a function of time with the temperature able to be lowered throughout the testing while data is collected, the improvement which comprises the spring having a shear stress of at least about 90 Pa.

14. The instrument of claim 13, wherein the shear stress is at least about 1000 Pa.

15. The instrument of claim 14, wherein the shear stress is at least about 4000 Pa.

16. The instrument of claim 15, wherein the shear stress is at least about 5000 Pa.

17. The instrument of claim 16, wherein the shear stress is at least about 6000 Pa.

* * * * *